(12) United States Patent
Hart et al.

(10) Patent No.: US 11,737,964 B2
(45) Date of Patent: Aug. 29, 2023

(54) HAIR COLOR TONING COMPOSITIONS, METHODS OF USE, AND KITS

(71) Applicant: L'OREAL, Paris (FR)

(72) Inventors: Taylor Katherine Hart, New York, NY (US); Emma Howes, Lake Hiawatha, NJ (US); Melanie Crim, Picastaway, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/389,137

(22) Filed: Jul. 29, 2021

(65) Prior Publication Data

US 2023/0099740 A1    Mar. 30, 2023

(51) Int. Cl.

| | |
|---|---|
| *A61Q 5/10* | (2006.01) |
| *A61K 8/42* | (2006.01) |
| *A61K 8/92* | (2006.01) |
| *A61Q 5/12* | (2006.01) |
| *A61Q 5/00* | (2006.01) |
| *A61K 8/365* | (2006.01) |
| *A61K 8/73* | (2006.01) |
| *A61K 8/34* | (2006.01) |

(52) U.S. Cl.
CPC ............... *A61K 8/42* (2013.01); *A61K 8/342* (2013.01); *A61K 8/365* (2013.01); *A61K 8/73* (2013.01); *A61K 8/922* (2013.01); *A61Q 5/002* (2013.01); *A61Q 5/10* (2013.01); *A61Q 5/12* (2013.01); *A61K 2800/34* (2013.01); *A61K 2800/4324* (2013.01); *A61K 2800/48* (2013.01)

(58) Field of Classification Search
CPC .......... A61K 8/42; A61K 8/342; A61K 8/365; A61K 8/73; A61K 8/922; A61K 2800/34; A61K 2800/4324; A61K 2800/48; A61Q 5/002; A61Q 5/10; A61Q 5/12

USPC .......................................................... 8/405
See application file for complete search history.

(56) References Cited

U.S. PATENT DOCUMENTS

| | | | |
|---|---|---|---|
| 5,708,151 A | 1/1998 | Möckli | |
| 9,192,556 B2 | 11/2015 | Weser et al. | |
| 2018/0116942 A1* | 5/2018 | Mahadeshwar | ........ A61K 8/365 |
| 2019/0029949 A1* | 1/2019 | Ceballos | ................ A61K 8/922 |

FOREIGN PATENT DOCUMENTS

| | | |
|---|---|---|
| EP | 0714954 A2 | 6/1996 |
| FR | 3104983 A1 | 6/2021 |
| WO | 95/01772 A1 | 1/1995 |
| WO | 95/15144 A1 | 6/1995 |
| WO | 2021/123329 A1 | 6/2021 |

OTHER PUBLICATIONS

Mintel: "7 Days Coloring Hair Treatment" Able C&C, Record ID 6016629, XP055926528 dated Oct. 1, 2018.*
Porter, M.R., "Handbook of Surfactants," published by Blackie & Son (Glasgow and London), 1991, pp. 116-178.
French Search Report and Written Opinion for counterpart Application No. 2109674, dated Jun. 1, 2022.

* cited by examiner

*Primary Examiner* — Eisa B Elhilo
(74) *Attorney, Agent, or Firm* — The Marbury Law Group, PLLC

(57) ABSTRACT

The present disclosure relates to hair color toning compositions comprising (a) one or more vegetable oils: (b) one or more solid fatty alcohols; (c) one or more nonionic surfactants; (d) one or more non-silicone shine enhancers; (e) one or more amidoamines; (f) one or more acids; (g) one or more direct dyes; and (g) water. Kits comprising the hair color toning compositions and methods of treating hair using the hair color toning compositions are also disclosed.

27 Claims, No Drawings

HAIR COLOR TONING COMPOSITIONS, METHODS OF USE, AND KITS

TECHNICAL FIELD

The present disclosure generally relates to compositions and methods for imparting color and/or tone to the hair while providing hair care benefits to hair, as well as kits comprising the compositions.

BACKGROUND

It is known that consumers desire to use cosmetic and care compositions that enhance the appearance of keratinous substrates such as hair, e.g., by changing the color, style, and/or shape of the hair, and/or by imparting various properties to hair, such as shine and conditioning.

Many of the known compositions and processes for enhancing the appearance of the hair involve chemical treatment of the hair. The process of changing the color of hair, for example, can involve depositing an artificial color onto the hair which provides a different shade or color to the hair, and/or lifting the color of the hair, such as lightening the color of dark hair to lighter shades.

The process of lifting the color of hair, also known as lightening or bleaching the hair, generally requires the use of compositions that comprise at least one oxidizing agent. Lightening or lifting the color of the hair is typically evaluated by the variation in tone height before and after the application of a hair color toning composition onto hair. This variation corresponds to the degree or level of lightening or lift. The notion of "tone" is based on the classification of the natural shades, one tone separating each shade from the shade immediately following or preceding it, which is well known to hairstyling professionals. The tone heights or levels range from 1 (black) to 10 (light blond), one unit corresponding to one tone; thus, the higher the number, the lighter the shade or the greater the degree of lift.

Typically, following a hair lightening or bleaching process, consumers also deposit color into or onto the bleached hair in order to obtain a hair color that is different than either the color of the hair prior to bleaching, or the color of the bleached hair. This process is conventionally referred to as "coloring" or "dyeing" the hair. The most common hair dyeing processes are permanent and semi-permanent or temporary hair dyeing. Permanent hair dyeing compositions uses oxidation dye precursors, which are also known as primary intermediates or couplers. These oxidation dye precursors are colorless or weakly colored compounds which, when combined with oxidizing products, give rise to colored complexes by a process of oxidative condensation. The permanent hair dye compositions also contain ammonia or other alkalizing agents which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair.

On the other hand, semi-permanent or temporary hair dyeing compositions typically use pigments, liposoluble dyes, or direct dyes chosen from acidic (anionic), basic (cationic), or neutral direct dyes which are deposited onto the hair fiber to impart color to the hair. In some instances, such dyeing compositions can also be combined with an oxidizing composition.

While the processes above are effective in altering the color of the hair, most of these chemical treatments can damage the hair fibers leading to decreased strength of the hair, as well as negatively affecting the sensorial properties of the hair, such as the smoothness, shine, and feel. Furthermore, as time passes after a hair lightening and/or dyeing process, the consumer often sees a change in the color of the hair, for example a fading or dulling of the original color or a change to a more brassy color, which changes may be caused by regular hair washing and/or styling, or by environmental factors such as expose to UV light from the sun. Thus, in order to either reduce or avoid these drawbacks or provide additional benefits to improve the sensorial properties of the hair while altering the color of the hair, the use of new and additional components and treatment compositions for use before, during, or after, or as a complement to, processes for altering the color of the hair are needed.

However, the choice of such components or treatments could pose difficulties insofar as they cannot be detrimental to other cosmetic attributes such as ease and uniformity of application, rheology or viscosity properties and stability of the compositions, color deposit and target shade formation, and/or result in more disadvantages such as increased damage or a less healthy look to the hair. It would therefore be desirable to provide the consumer with compositions and methods that can treat the hair, e.g. tone the color of hair and/or deposit color onto hair in an effective manner, while providing or maintaining other cosmetic and sensorial properties such as shine, conditioning, fiber strength, improved wet combing or detangling properties of hair, and/or a healthy appearance to the hair, but avoiding or minimizing damage to the hair.

SUMMARY

The present disclosure relates to compositions and methods for treating hair, such as refreshing or toning the color of the hair, in particular, human hair of the head. Typically, the hair has been previously lightened or colored, and may, for example, have a tone level ranging from 4 to 10. The hair color toning/refresher compositions of the disclosure are particularly useful for toning or providing color vibrancy effects to hair, as well as styling and conditioning benefits to the hair, for example, imparting shine, smoothness, softness, sealed ends, and discipline to the hair.

The hair color toning compositions include natural ingredients such as vegetable-derived oils; synthetic materials, such as silicones are not required. Thus, the hair color toning compositions may be natural products that do not include synthetic ingredients. Even without synthetic ingredients, such as silicones, the hair color toning compositions are stable, have a fluid viscosity, and provide superior performance. In comparison to typical silicone-based products and other comparative formulations, the instant hair color toning compositions provide better conditioning, smoothness, shape, shine, and discipline to hair with a cleaner, lightweight feel.

The hair color toning compositions of the disclosure may include:
  (a) one or more vegetable oils;
  (b) one or more solid fatty alcohols;
  (c) one or more nonionic surfactants;
  (d) one or more non-silicone shine enhancers;
  (e) one or more amidoamines:
  (f) one or more acids;
  (g) one or more direct dyes; and
  (h) water.

The hair color toning/refresher compositions typically have a fluid viscosity, for example a viscosity of greater than about 12 DU (units of deflection), for example from about 12 DU to about 25 DU, or more preferably from about 12 DU to about 20 DU. Additionally, the hair color toning compositions typically have a low pH (e.g., less than 7, for instance, a pH of about 2 to about 6, or about 3 to about 5.5). Also, as mentioned above, the hair color toning compositions do not require synthetic compounds including synthetic silicone compounds. Thus, the hair color toning compositions may be free or essentially free of silicones.

Non-limiting examples of vegetable oils include coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, or mixtures of any two or more of the foregoing. In some cases, the hair color toning composition includes at least coconut oil. Also useful is a combination of coconut oil and soybean oil.

Non-limiting examples of solid fatty alcohols include cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, or mixtures of any two or more of the foregoing.

Many nonionic surfactants are known and useable in the hair color toning compositions. Nonetheless, in some cases, the hair color toning compositions may include one or more esters of polyols with fatty acids or alkoxylated derivatives thereof. Non-limiting examples include glyceryl distearate, glyceryl hydroxystearate, glyceryl laurate, glyceryl linoleate, glyceryl myristate, glyceryl oleate, glyceryl stearate, an ethoxylated derivate thereof, or mixtures of any two or more of the foregoing.

Non-silicone shine enhancers may include, for example, liquid fatty alcohols. Non-limiting examples of liquid fatty alcohols include 2-octyldodecanol, isostearyl alcohol, 2-hexyldecanol, 2-heptyldecanol, 2-octyldecanol, caproic alcohol (1-hexanol), enanthic alcohol (1-heptanol), caprylic alcohol (1-octanol), pelargonic alcohol (1-nonanol), capric alcohol (1-decanol), lauryl alcohol (1-dodecanol), or mixtures of any two or more of the foregoing.

Non-limiting examples of amidoamines include oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, or mixtures of any two or more of the foregoing.

Non-limiting examples of acids include glycolic acid, lactic acid, malic acid, tartaric acid, citric acid, ascorbic acid, mandelic acid, azelaic acid, glyceric acid, tartronic acid, gluconic acid, benzylic acid, pyruvic acid, 2-hydroxybutyric acid, salicylic acid, trichloroacetic acid, or mixtures of any two or more of the foregoing.

Non-limiting examples of direct dyes include HC Blue No. 15, Basic Violet 2, Basic Red 51, HC Violet No. 2, Basic Yellow 87, Basic Orange 31, HC Blue 2, Basic Yellow 57, Ext. Violet 2, Acid Red 33, Basic Brown 17, 2-nitro-5-glyceryl methylaniline, 3-methylamino-4-nitrophenoxyethanol, or mixtures of any two or more of the foregoing.

The hair color toning compositions are useful in treating hair, for example, methods for coloring or toning while conditioning hair or for providing color/tone or anti-brassiness effects and conditioning benefits to hair. Non-limiting examples of conditioning benefits include imparting shine, color vibrancy, smoothness, softness, and discipline to the hair. The hair color toning compositions may also be used to improve frizz control (i.e., to reduce frizz), provide end seal of split ends or reduce the development of split ends, and enhance root lift. The methods typically include applying a hair color toning composition to the hair, allowing the composition to remain on the hair for a period of time, and rinsing the hair color toning composition from the hair. For example, the hair color toning composition may be allowed to remain on the hair for about 1 minute to about 20 minutes, about 3 minutes to about 15 minutes, or about 5 minutes to about 10 minutes.

In some cases, the hair color toning compositions are applied to the hair shortly after the hair has been cleansed or shampooed, for example, while the hair is still wet or damp. After the hair color toning composition has remained on the hair for a period of time, it is rinsed from the hair and the hair may optionally be further treated with, for example, a typical conditioning or hair treatment compositions (a conditioner or masque) and/or styled. Alternatively, a hair color toning composition may be applied to the hair before the hair is cleansed or shampooed. For example, the hair color toning composition may be applied to the hair (wet or dry) and allowed to remain on the hair for a period of time and rinsed from the hair. After rinsing the hair color toning composition from the hair, the hair is cleansed or shampooed and optionally treated with a typical conditioning or masque composition (leave-in or rinse-off).

In some instances, the hair color toning compositions are particularly useful as an interim treatment, e.g., a treatment to the hair immediately after shampooing the hair but before conditioning the hair or immediately after chemically treating the hair but before cleansing or shampooing the hair in order to improve the tone of the hair or to provide anti-brassiness effects to hair. For example, after rinsing a chemical treatment composition from the hair, a hair color toning composition according to the instant disclosure can be applied to the hair and allowed to remain on the hair for a period of time and rinsed from the hair. After rinsing the hair color toning composition from the hair, the hair may be cleansed or shampooed, optionally treated with a conditioning composition (a conditioner or masque), and styled. The hair color toning composition is also particularly useful as an interim treatment between shampooing and conditioning. After a shampoo has been rinsed from the hair, for example, while the hair is still damp, a hair color toning composition may be applied to the hair and allowed to remain on the hair for a period of time. After optionally rinsing the hair color toning composition from the hair, the hair is conditioned (i.e., a conditioner is applied to the hair). After rinsing the conditioner from the hair, the hair may be styled, as desired.

The hair color toning compositions may be included in a kit, for example, a kit comprising a hair color toning composition, a shampoo, and optionally a conditioner or masque treatment. The hair color toning composition, the shampoo, and the optional conditioner are separately contained or separately packaged.

DETAILED DESCRIPTION

The present disclosure relates to hair color toning compositions, methods of using the hair color toning compositions, and kits comprising the hair color toning compositions. The terms "hair color toning composition," "hair color refreshing composition," "hair color toning/refreshing composition," and variations thereof, relates to a composition according to the present disclosure that is applied to the hair to deposit color onto the hair, to refresh or liven the color of the hair, and/or to tone the color of the hair in order to provide anti-brassiness color effects to color-treated or dyed hair.

The hair color toning compositions according to the disclosure may also improve the hair's cosmetic characteristics. Non-limiting, desirable cosmetic properties that may be imparted to the hair include conditioning and style benefits such as imparting shine, color vibrancy, smoothness, softness, improved wet combing or detangling, and/or discipline to the hair. Hair treated with the hair color toning compositions becomes moisturized, soft, silky, and/or is easy to detangle regardless of whether the hair is wet or dry. Compositions The hair color toning compositions of the disclosure typically include (a) one or more vegetable oils; (b) one or more solid fatty alcohols; (c) one or more nonionic surfactants; (d) one or more non-silicone shine enhancers; (e) one or more amidoamines; (f) one or more acids; (g) one or more direct dyes; and (h) water.

The hair color toning compositions typically have a fluid viscosity, for example a viscosity of at least 12 DU (Units of Deflection or "Deflection Units") (about 22 mPa·s) at 25° C., when measured 200 RPM for 30 seconds using a spindle #2 (Rheomat 180). In some instances, the viscosity may be about 12 to about 30 DU, about 12 to about 25 DU, or about 12 to about 20 DU.

The hair color toning compositions typically have a pH of less than 7. In some cases, the pH of the hair color toning compositions may be about 2 to about 6, about 3 to about 5.5, about 3.5 to about 5.5, or about 3.7 to about 5.2.

The hair color toning compositions do not require synthetic compounds including synthetic silicone compounds. Thus, the hair color toning compositions may be free or essentially free of silicones and/or free or essentially free of other synthetic components. Thus, in some instances, the hair color toning compositions according to the disclosure may be "natural hair color toning compositions." The term "natural" may be used in the present disclosure to specify that the composition is free or essentially free of synthetic ingredients. The term "natural" may also be used in the present disclosure to specify that the composition contains natural-based ingredients such as plant- or vegetable-derived ingredients, for example, the vegetable oils of the disclosure.

As noted previously, the hair color toning compositions of the instant disclosure typically also provide styling and/or conditioning benefits to the hair. Many typical products that provide conditioning benefits to hair include cationic surfactants selected from quaternary ammonium compounds (e.g., behentrimonium chloride, cetrimonium chloride, behentrimonium methosulfate) and/or quaternary ammonium polymers (e.g., polyquaterniums). The hair color toning compositions of the instant disclosure, however, employ one or more amidoamine compounds which help provide conditioning benefits; amidoamine compounds can function as a cationic conditioning compound depending on the final pH of the hair color toning compositions of the instant disclosure. Thus, cationic compounds selected from quaternary ammonium compounds (e.g., behentrimonium chloride, cetrimonium chloride, behentrimonium methosulfate) and/or quaternary ammonium polymers (e.g., polyquaterniums) are not required in the hair color toning compositions, and therefore in at least some embodiments, the hair color toning compositions of the instant disclosure may be free or essentially free of cationic compounds selected from quaternary ammonium compounds (e.g., behentrimonium chloride, cetrimonium chloride, behentrimonium methosulfate) and/or quaternary ammonium polymers (e.g., polyquaterniums).

As used herein, a vegetable oil is an oil derived from a plant, for example, oils from seeds or fruits. Non-limiting examples of vegetable oils include coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, and a mixture thereof. In some cases, the hair color toning composition includes at least coconut oil. Also useful is a combination of coconut oil and soybean oil.

In an embodiment, the vegetable oils in the compositions of the present disclosure are chosen from coconut oil, soybean oil, or a mixture thereof.

In an embodiment, the vegetable oils in the composition of the present disclosure comprise coconut oil.

In an embodiment, the vegetable oils in the composition of the present disclosure comprise soybean oil.

Typically, the hair color toning compositions include about 0.01 to about 5%, such as about 0.1 to about 3% of one or more vegetable oils by weight, based on the total weight of the hair color toning composition. The total amount of the one or more vegetable oils may be about 1 to about 2.5%, about 1.5 to about 3%, or about 1.5 to about 2.5% by weight, based on the total weight of the hair color toning composition.

The solid fatty alcohol(s) may be crystalline, amorphous or pasty. The solid fatty alcohol(s) are solid at room temperature (25° C.) and at atmospheric pressure (1 atm) and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, chloroform, benzene or liquid petroleum jelly) to at least 1% by weight.

In some cases, the solid fatty alcohols may have a melting point of greater than or equal to 28° C. and have a viscosity, at a temperature of 40° C. and at a shear rate of 1 s$^{-1}$, of greater than or equal to 1 Pa·s. Furthermore, in some cases, the melting point of the fatty alcohols ranges from 30° C. to 250° C., such as from 32° C. to 150° C. or such as from 35° C. to 150° C.

The melting points may be measured by DSC or on a Kofler bench. The melting point may be measured by differential calorimetric analysis (DSC) with a temperature rise of 10° C. per minute. The melting point is then the temperature corresponding to the top of the melting endotherm peak obtained during the measurement.

The viscosity measurements may be taken at a temperature of about 40° C. using an RS600 rheometer from Thermoelectron.

The solid fatty alcohols of the present invention are chosen from saturated or unsaturated, linear or branched, preferably linear and saturated, (mono) alcohols comprising from 8 to 40 carbon atoms, such as from 10 to 30 carbon atoms, or such as from 12 to 24 carbon atoms. The solid fatty alcohols preferably have the structure of formula: R—OH in which R especially denotes a C6-C60, for example, C8-C60, preferably C10-C50 or even C12-C30 alkyl group, R possibly being substituted with one or more hydroxyl groups, R possibly being branched.

Non-limiting examples of solid fatty alcohols include myristyl alcohol, cetyl alcohol, stearyl alcohol, behenyl alcohol, and mixtures thereof. Other suitable non-limiting examples of solid fatty alcohols include branched solid fatty alcohols chosen from 2-dodecylhexadecanol, 2-tetradecyl-1-octadecanol, 2-tetradecyl-1-eicosanol, 2-hexadecyl-1-octadecanol and 2-hexadecyl-1-eicosanol, and mixtures thereof.

The solid fatty alcohol may represent a mixture of fatty alcohols, which means that several species of fatty alcohol may coexist, in the form of a mixture, in a commercial product. The solid fatty alcohols of the invention are preferably non-oxyalkylenated and/or non-glycerolated. These fatty alcohols may be constituents of animal or plant waxes.

In some instances, the solid fatty alcohols are chosen from cetyl alcohol, stearyl alcohol and mixtures thereof (cetylstearyl alcohol or cetearyl alcohol).

The total amount of the solid fatty alcohols is typically about 0.01 to about 5%, such as about 1 to about 4% by weight, based on the total weight of the hair color toning composition. The total amount of the one or more solid fatty alcohol may be about 2 to about 3.5%, about 2.5 to about 4%, or about 2.5 to about 3.5% by weight, based on the total weight of the hair color toning composition.

Many nonionic surfactants are known and may be useful in the hair color toning compositions of the instant disclosure. Non-limiting classes of nonionic surfactants include esters of polyols with fatty acids and alkoxylated derivatives thereof, alkylpolyglucosides, sucrose esters, alkoxylated ethers of fatty acids and glucose or alkylglucose, esters of fatty acids and glucose or alkylglucose, sorbitol esters of fatty acids and alkoxylated derivatives thereof, alkoxylated fatty alcohols (for example, ethoxylated fatty alcohols), alkanolamides, and a mixture thereof. A more exhaustive list of anionic surfactants that may be included in the hair color toning compositions is provided later, under the heading "Nonionic Surfactants."

In some instances, the hair color toning compositions include one or more esters of polyols with fatty acids or alkoxylated derivatives thereof as at least one of the one or more nonionic surfactants. Non-limiting examples include glyceryl distearate, glyceryl hydroxystearate, glyceryl laurate, glyceryl linoleate, glyceryl myristate, glyceryl oleate, glyceryl stearate, an ethoxylated derivate thereof, and a mixture thereof. In some cases, glyceryl stearate is particularly useful.

In an embodiment, the nonionic surfactants in the composition of the present disclosure are chosen from glyceryl oleate, glyceryl stearate, or a mixture thereof.

In an embodiment, the nonionic surfactants in the composition of the present disclosure comprise glyceryl oleate.

In an embodiment, the nonionic surfactants in the composition of the present disclosure comprise glyceryl stearate.

The total amount of the one or more nonionic surfactants can range from about 0.05 to about 15%, based on the total weight of the hair color toning composition. The total amount of the one or more nonionic surfactants may be from about 0.05 to about 10%, about 0.1 to about 5%, or about 0.1 to about 4%, or about 0.15 to about 3%, or about 0.15 to about 2.5%, or about 0.15 to about 2%, or about 0.15 to about 1.5% by weight, based on the total weight of the hair color toning composition Non-silicone shine enhancers are compounds that impart, improve, or enhance shine to hair. The compounds themselves may be responsible for the shine or may interact with other compounds in the hair color toning composition to improve or enhance the shine of hair.

In some cases, one or more of the shine enhancers is a liquid fatty alcohol such as those chosen from saturated or unsaturated, linear or branched alcohols comprising from 6 to 50 carbon atoms and preferably from 8 to 30 carbon atoms. The liquid fatty alcohol(s) are liquid at room temperature (25° C.) and at atmospheric pressure (1 atm) and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, or liquid petroleum jelly or other cosmetically acceptable organic solvent) to at least 1% by weight. Mention may be made, for example, of octyldodecanol, 2-butyloctanol, 2-hexyldecanol, 2-undecylpentadecanol, oleyl alcohol or linoleyl alcohol. The saturated liquid fatty alcohols can be branched. They can optionally comprise, in their structure, at least one aromatic or non-aromatic ring. They can be acyclic. Among liquid saturated fatty alcohols, octyldodecanol, isostearyl alcohol and 2-hexyldecanol can be cited.

The unsaturated liquid fatty alcohols may exhibit, in their structure, at least one double or triple bond and preferably one or more double bonds. When several double bonds are present, there are preferably 2 or 3 of them and they can be conjugated or unconjugated. These unsaturated fatty alcohols can be linear or branched. They can optionally comprise, in their structure, at least one aromatic or non-aromatic ring. They can be acyclic. Among the liquid unsaturated fatty alcohols, oleyl alcohol, linoleyl alcohol, linolenyl alcohol and undecylenyl alcohol may be mentioned.

The total amount of the one or more non-silicone shine enhancers may vary but is typically about 0.01 to about 10%, based on the total weight of the hair color toning composition. In some instances, the total amount of the one or more non-silicone shine enhancers is about 0.01 to about 8%, about 0.01 to about 5%, about 0.01 to about 3%, about 0.1 to about 10%, about 0.1 to about 8%, about 0.1 to about 5%, or about 0.1 to about 3% by weight, based on the total weight of the hair color toning composition.

Amidoamines are a class of chemical compounds that are formed from fatty acids and diamines. Non-limiting examples of amidoamines include those of the following formula:

wherein R is a hydrocarbon radical containing at least 6 carbon atoms; R' is a divalent hydrocarbon radical containing less than 6 carbon atoms; and R" is H or a hydrocarbon radical containing less than 6 carbon atoms. In addition, R can be linear or branched, acyclic or cyclic, saturated or unsaturated, aliphatic or aromatic, substituted or unsubstituted, and R" can be linear or branched, acyclic or cyclic, saturated or unsaturated, substituted or unsubstituted. Typically, R is a linear or branched, acyclic alkyl or alkenyl group or an alkyl phenyl group, R' is a divalent hydrocarbon radical containing 2 or 3 carbon atoms, and, R" is a linear or branched, acyclic alkyl or alkenyl group. In some cases, R" is H or a methyl group.

Non-limiting examples of amidoamines include oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicamidopropyl dimethylamine, olivamidopropyl dimethylamine, palmitamidopropyl dimethylamine, stearamidoethyldiethylamine, and a mixture thereof. In some cases, brassicamidopropyl dimethylamine may be particularly useful.

In an embodiment, the amidoamine in the composition of the present disclosure comprises brassicamidopropyl dimethylamine.

In an embodiment, the amidoamine in the composition of the present disclosure comprises stearamidopropyl dimethylamine.

The total amount of the one or more amidoamines in the hair color toning compositions can vary but is typically about 0.1 to about 15%, based on the total weight of the hair color toning composition. In some instances, the total amount of the one or more amidoamines may be about 0.1 to about 12%, about 0.1 to about 10%, about 0.1 to about 8%, about 0.1 to about 6%, about 0.1 to about 5%, about 1 to about 15%, about 1 to about 12%, about 1 to about 10%, about 1 to about 8%, about 1 to about 6%, or about 1 to about 5% by weight, based on the total weight of the hair color toning composition.

The hair color toning compositions typically include one or more acids. The acids may be used, for example, to neutralize the one or more amidoamines and/or to achieve a desired pH. Non-limiting examples of useful acids include glycolic acid, lactic acid, malic acid, tartaric acid, citric acid, ascorbic acid, mandelic acid, azelaic acid, glyceric acid, tartronic acid, gluconic acid, benzylic acid, pyruvic acid, 2-hydroxybutyric acid, salicylic acid, trichloroacetic acid, and a mixture thereof.

The acids are typically non-polymeric and may have one (mono), two (di), or three (tri) carboxylic acid groups (—COOH). The non-polymeric mono, di, and tricarboxylic acids, and/or salts thereof, typically have a molecular weight of less than about 500 g/mol, less than about 400 g/mol, or less than about 300 g/mol.

Non-limiting examples of monocarboxylic acids include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof.

Non-limiting examples of dicarboxylic acids include oxalic acid, malonic acid, malic acid, glutaric acid, citraconic acid, succinic acid, adipic acid, tartaric acid, fumaric acid, sebacic acid, azelaic acid, dodecanedioic acid, phthalic acid, isophthalic acid, terephthalic acid, 2,6-naphthalene dicarboxylic acid, a salt thereof, and a mixture thereof.

Non-limiting examples of tricarboxylic acids include citric acid, isocitric acid, aconitric acid, propane-1,2,3-tricarboxylic acid, benzene-1,3,5-tricarboxylic acid, a salt thereof, and a mixture thereof.

The total amount of the one or more acids may vary but s typically about 0.01 to about 5%, based on the total weight of the hair color toning composition. In some cases, the total amount of the one or more acids is about 0.01 to about 4%, about 0.01 to about 3%, about 0.01 to about 2%, about 0.05 to about 5%, about 0.05 to about 4%, about 0.05 to about 3%, about 0.05 to about 2%, about 0.1 to about 5%, about 0.1 to about 4%, about 0.1 to about 3%, about 0.1 to about 2% or about 0.1 to about 1% by weight, based on the total weight of the hair color toning composition.

The hair color toning compositions include one or more direct dyes. Non-limiting examples of suitable direct dyes include synthetic or natural direct dyes, for example, chosen from anionic, cationic, and nonionic species, or mixtures thereof. In certain embodiments, the hair color toning compositions are free or substantially free of oxidation dyes and/or couplers.

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

The total amount of the one or more direct dyes may vary, but the direct dyes are present in a total amount sufficient to impart color effects to the hair, e.g. to tone and/or refresh the color of the hair, as opposed to coloring the product only. For example, the total amount of direct dye(s) may range from about 0.001 to about 10%, about 0.01 to about 3%, or about 0.05 to about 1% by weight, based on the total weight of the hair color toning composition.

In one embodiment, the hair color toning composition may include:
(a) about 0.01 to about 5%, such as about 0.1 to about 3% of one or more vegetable oils, for example coconut oil, soybean oil, or a mixture thereof;
(b) about 0.01 to about 5%, such as about 1 to about 4% of one or more straight chain fatty alcohols, for example cetearyl alcohol;
(c) 1% or less of one or more esters of polyols with fatty acids or alkoxylated derivatives thereof, for example, glyceryl distearate, glyceryl hydroxystearate, glyceryl laurate, glyceryl linoleate, glyceryl myristate, glyceryl oleate, glyceryl stearate, an ethoxylated derivate thereof, or a mixture thereof;
(d) about 0.1 to about 5% of one or more non-silicone shine enhancers, wherein the non-silicone shine enhancer is a branched chain fatty alcohol, for example, 2-octyldodecanol;
(e) about 1 to about 15%, about 1 to about 10%, or about 1 to about 5% of one or more amidoamines of the formula:

wherein R is a linear or branched, acyclic alkyl or alkenyl group or an alkyl phenyl group; R' is a divalent hydrocarbon radical containing less than 6 carbon atoms; and R" is H or a hydrocarbon radical containing less than 6 carbon atoms, for example, brassicamidopropyl dimethylamine;
(f) about 0.01 to about 5%, about 0.1 to about 5%, or about 0.1 to about 2% of one or more non-polymeric mono-, di-, or tricarboxylic acids;
(g) about 0.01 to about 3%, about 0.02 to about 2.5%, about 0.03 to about 2%, about 0.04 to about 1.5%, about 0.05 to about 1%, about 0.05 to about 0.8%, of one or more direct dyes; and
(h) about 60 to about 95%, about 70 to about 95%, or about 80 to about 95% of water;
wherein the pH of the composition ranges from about 2 to about 6, or about 3 to about 5.5, all amounts being by weight, based on the total weight of the hair color toning composition.

In various embodiments, the compositions of the disclosure impart shades or colors such as violet, blue, green, copper, gold and/or red to the hair. Accordingly, in various embodiments, the one or more direct dyes may be chosen from HC Blue No. 15, Basic Violet 2, Basic Red 51, HC Violet No. 2, Basic Yellow 87, Basic Orange 31, HC Blue 2, Basic Yellow 57, Ext Violet 2, Acid Red 33, Basic Brown 17, 2-nitro-5-glyceryl methylaniline, 3-methylamino-4-nitrophenoxyethanol, or mixtures of any two or more of the foregoing.

In one embodiment, the hair color toning composition comprises Basic Red 51 and HC Violet 2. For example, the hair color toning composition may comprise from about 0.0001% to about 0.002%, such as about 0.0005% to about 0.0015% Basic Red 51, and from about 0.01% to about 0.5%, such as about 0.06% to about 0.25% HC Violet 2, and the pH of the hair color toning composition may range from about 4.2 to about 5.5, such as about 4.5 to about 5.1.

In a further embodiment, the hair color toning composition comprises Basic Red 51 and Basic Yellow 87. For example, the hair color toning composition may comprise from about 0.01% to about 0.5%, such as about 0.08% to about 0.25% Basic Red 51, and from about 0.01% to about 0.5%, such as about 0.08% to about 0.25% Basic Yellow 87, and the pH of the hair color toning composition may range from about 3.8 to about 5.3, such as about 4 to about 5. In yet a further embodiment, the hair color toning composition comprises Basic Yellow 57 and Basic Brown 17. For example, the hair color toning composition may comprise from about 0.005% to about 0.15%, such as about 0.01% to about 0.1% Basic Yellow 57, and from about 0.001% to about 0.02%, such as about 0.005% to about 0.12% Basic Brown 17, and the pH of the hair color toning composition may range from about 3.8 to about 5.3, such as about 4 to about 5.

In a still further embodiment, the hair color toning composition comprises HC Blue No. 2, Basic Yellow 87, 2-nitro-5-glyceryl methylaniline, and Basic Orange 31. For example, the hair color toning composition may comprise from about 0.005% to about 0.3%, such as about 0.01% to about 0.15% HC Blue No. 2, from about 0.05% to about 0.5%, such as about 0.1% to about 0.35% Basic Yellow 87, from about 0.005% to about 0.15%, such as about 0.01% to about 0.1% 2-nitro-5-glyceryl methylaniline, and from about 0.05% to about 0.5%, such as about 0.1% to about 0.35% Basic Orange 31, and the pH of the hair color toning composition may range from about 3.8 to about 5.3, such as about 4 to about 5.

In a further embodiment still, the hair color toning composition comprises HC Blue No. 2, Basic Brown 17, Basic Red 51, 2-nitro-5-glyceryl methylaniline, and 3-methylamino-4-nitrophenoxyethanol. For example, the hair color toning composition may comprise from about 0.005% to about 0.3%, such as about 0.01% to about 0.15% HC Blue No. 2, from about 0.05% to about 0.7%, such as about 0.15% to about 0.5% Basic Brown 17, from about 0.001% to about 0.02%, such as about 0.005% to about 0.12% Basic Red 51, from about 0.05% to about 0.6%, such as about 0.1% to about 0.4% 2-nitro-5-glyceryl methylaniline, and from about 0.005% to about 0.15%, such as about 0.01% to about 0.1% 3-methylamino-4-nitrophenoxyethanol, and the pH of the hair color toning composition may range from about 3.8 to about 5.3, such as about 4 to about 5.

In a further embodiment, the hair color toning composition comprises HC Blue No. 2, Ext. Violet 2, HC Blue No. 15, and 2-nitro-5-glyceryl methylaniline. For example, the hair color toning composition may comprise from about 0.005% to about 0.3%, such as about 0.01% to about 0.15% HC Blue No. 2, from about 0.005% to about 0.2%, such as about 0.01% to about 0.15% Ext. Violet 2, from about 0.0001% to about 0.001% HC Blue No. 15, and from about 0.0005% to about 0.01%, such as about 0.001% to about 0.008% 2-nitro-5-glyceryl methylaniline, and the pH of the hair color toning composition may range from about 3.8 to about 5.3, such as about 4 to about 5.

In still further embodiments, the hair color toning composition comprises HC Blue No. 2, Ext. Violet 2, HC Blue No. 15, and 2-nitro-5-glyceryl methylaniline. For example, the hair color toning composition may comprise from about 0.005% to about 0.2%, such as about 0.01% to about 0.15% HC Blue No. 2, from about 0.005% to about 0.5%, such as about 0.01% to about 0.35% Ext. Violet 2, from about 0.0001% to about 0.01%, such as about 0.0008% to about 0.008% HC Blue No. 15, and from about 0.0005% to about 0.01%, such as about 0.001% to about 0.006% 2-nitro-5-glyceryl methylaniline, and the pH of the hair color toning composition may range from about 3.8 to about 5.3, such as about 4 to about 5.

In further embodiments, the hair color toning composition comprises HC Blue No. 2, Basic Yellow 87, and HC Blue No. 15. For example, the hair color toning composition may comprise from about 0.01% to about 1.5%, such as about 0.1% to about 1% HC Blue No. 2, from about 0.005% to about 0.5%, such as about 0.01% to about 0.35% Basic Yellow 87, and from about 0.001% to about 0.1%, such as about 0.005% to about 0.08% HC Blue No. 15, and the pH of the hair color toning composition may range from about 3.5 to about 4.5, such as about 3.8 to about 4.2.

In yet further embodiments, the hair color toning composition comprises Basic Yellow 87, Basic Yellow 57, and HC Blue No. 15. For example, the hair color toning composition may comprise from about 0.005% to about 0.15%, such as about 0.01% to about 0.06% Basic Yellow 87, from about 0.01% to about 0.5%, such as about 0.08% to about 0.3% Basic Yellow 57, and from about 0.005% to about 0.3%, such as about 0.01% to about 0.15% HC Blue No. 15, and the pH of the hair color toning composition may range from about 3.5 to about 4.5, such as about 3.8 to about 4.2.

In still further embodiments, the hair color toning composition comprises HC Violet No. 2, Basic Yellow 87, and Basic Red 51. For example, the hair color toning composition may comprise from about 0.001% to about 0.02%, such as about 0.005% to about 0.12% HC Violet No. 2, from about 0.001% to about 0.03%, such as about 0.005% to about 0.02% Basic Yellow 87, and from about 0.0001% to about 0.0015%, such as about 0.0005% to about 0.001%

Basic Red 51, and the pH of the hair color toning composition may range from about 3.8 to about 5.3, such as about 4 to about 5.

The hair color toning composition has a fluid viscosity, for example a viscosity of less than 30 DU at 25° C., using a spindle #2, such as from about 12 DU to about 25 DU, or about 12 DU to about 20 DU.

Additionally, the hair color toning composition has a pH of less than 7. In some cases, the pH of the hair color toning composition may be about 2 to about 6, about 3 to about 6, or about 3 to about 5 or about 3 to about 4. For example, the pH may range from about 3.5 to about 4.5, such as about 3.7 to about 4.3, or about 3.8 to about 4.2. In a further example, the pH may range from about 4.0 to about 5.5, such as about 4.3 to about 5.3, or about 4.5 to about 5.1. In yet a further example, the pH may range from about 3.5 to about 5.5, such as about 3.8 to about 5.2, or about 4 to about 5. In various embodiments, the hair color toning compositions may have a pH of about any of the following: 2, 2.5, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5 5.1, 5.2, 5.3, 5.4, 5.5, 5.6, 5.7, 5.8, 5.9, or 6.

The hair color toning composition does not require synthetic compounds including synthetic silicone compounds. Thus, the hair color toning composition may be free or essentially free of silicones and/or free or essentially free of other synthetic components. Accordingly, the hair color toning composition may be a natural hair color toning composition. Moreover, the hair color toning composition may optionally be free or essentially free of cationic compounds selected from quaternary ammonium compounds (e.g., behentrimonium chloride, cetrimonium chloride, behentrimonium methosulfate) and quaternary ammonium polymers (e.g., polyquaterniums). Finally, the hair color toning compositions may optionally be free or essentially free of alkoxylated (including ethoxylated) compounds.

The hair color toning compositions are useful in treating hair, for example, methods for conditioning hair or for providing conditioning benefits to hair. Non-limiting examples of conditioning benefits include imparting shine, color vibrancy, smoothness, softness, and/or discipline to the hair. The hair color toning compositions may also be used to improve frizz control (i.e., to reduce frizz), provide end seal of split ends or reduce the development of split ends, and enhance root lift. The methods typically include applying a hair color toning composition to the hair, allowing the hair treatment composition to remain on the hair for a period of time, and rinsing the hair color toning composition from the hair.

For example, the hair color toning composition may be allowed to remain on the hair for about 5 seconds to about 30 minutes. The hair color toning composition may be allowed to remain on the hair for about 5 seconds to about 25 minutes, about 5 seconds to about 20 minutes about 5 seconds to about 15 minutes, about 5 seconds to about 10 minutes, about 30 seconds to about 30 minutes, about 30 seconds to about 25 minutes, about 30 seconds to about 20 minutes, about 30 seconds to about 15 minutes, about 30 seconds to about 10 minutes, about 1 minute to about 30 minutes, about 1 minute to about 25 minutes, about 1 minute to about 20 minutes, about 1 minute to about 15 minutes, about 1 minute to about 10 minutes. In particular, the hair color toning composition may be allowed to remain on the hair for about 2 minutes to about 15 minutes, or about 3 minutes to about 12 minutes, or about 5 minutes to about 10 minutes.

In some cases, the hair treatment compositions are applied to the hair shortly after the hair has been cleansed or shampooed, for example, while the hair is still wet or damp. After the hair color toning composition has remained on the hair for a period of time (e.g., about 5 minutes), it is rinsed from the hair and the hair may optionally be further treated with, for example, a typical conditioning composition (a conditioner) and/or styled. Alternatively, a hair color toning composition may be applied to the hair before the hair is cleansed or shampooed or chemically treated. For example, the hair color toning composition of the instant disclosure may be applied to the hair (wet or dry) as a pre-treatment composition and allowed to remain on the hair for a period of time (e.g., about 5 to 10 minutes) and rinsed from the hair. After rinsing the hair color toning from the hair, the hair is cleansed or shampooed and optionally treated with a typical conditioning composition (a conditioner).

In some instances, the hair color toning compositions are particularly useful as an interim treatment, e.g., a treatment to the hair immediately after shampooing the hair but before conditioning the hair or immediately after chemically treating the hair but before cleansing or shampooing the hair. For example, after rinsing a chemical treatment composition from the hair, a hair color toning composition according to the instant disclosure can be applied to the hair and allowed to remain on the hair for a period of time (e.g., about 5 to about 10 minutes) and rinsed from the hair. After rinsing the hair color toning composition from the hair, the hair may be cleansed or shampooed, optionally treated with a conditioning composition (a conditioner), and styled. The hair color toning composition is also particularly useful as an interim treatment between shampooing and conditioning. After a shampoo has been rinsed from the hair, for example, while the hair is still damp, a hair color toning composition may be applied to the hair and allowed to remain on the hair for a period of time. After optionally rinsing the hair color toning composition from the hair, the hair is conditioned (i.e., a conditioner is applied to the hair). After rinsing the conditioner from the hair, the hair may be styled, as desired.

The hair color toning compositions may be "layered" onto other hair color toning compositions that have already been applied to the hair. The term "layered" means that the hair color toning rinse is applied to the hair on which another composition has already been applied. For example, a shampoo, a conditioner, or a chemical hair treatment may first be applied to the hair. Without first rinsing the shampoo, the conditioner, or the chemical hair treatment from the hair, a hair color toning composition according to the instant disclosure may be layered on top of the shampoo, conditioner, or chemical hair treatment (which is already on the hair), and the hair color toning composition allowed to remain on the hair for a period of time before rinsing it, along with the underlying composition, from the hair.

In some instances, the hair color toning compositions are particularly useful either as a rinse-off or a leave-on post-treatment, e.g., a treatment to the hair immediately after treating the hair with a rinse-off conditioner or immediately after chemically treating the hair. For example, after rinsing a chemical treatment composition from the hair, a hair color toning composition according to the instant disclosure can be applied to the hair and allowed to remain on the hair for a period of time (e.g., about 5 to about 10 minutes) and rinsed from the hair. After rinsing the hair color toning composition from the hair, the hair may be cleansed or shampooed, optionally treated with a conditioning composition (a conditioner), and styled. In another example, after rinsing a conditioner from the hair, a hair color toning composition according to the instant disclosure can be applied to the wet, damp or dry hair as a leave-on composition and the hair may then be styled, as desired. In some cases, when used as a post-treatment composition, the hair color toning composition according to the instant disclosure can be used to protect the hair from damage from heat (for example, heat produced with the use of a blow dryer or flat iron or heating lamp or hood dryer on hair).

The hair color toning compositions may be included in a kit, for example, a kit comprising a hair color toning rinse, a shampoo, and optionally a conditioner. The hair color toning composition (rinse-off or leave-on), the shampoo, and the optional conditioner are separately contained or separately packaged. Kits according to the disclosure also include kits comprising a hair color toning composition and one or more chemical hair color toning compositions. Non-limiting examples of chemical hair color toning compositions include hair lightening compositions, hair coloring compositions, hair relaxing compositions, hair straightening compositions, and hair shaping compositions (e.g., compositions to permanently curl hair).

More exhaustive but non-limiting lists of components that are useful in the hair color toning compositions of the instant disclosure are presented below.

Solid Fatty Alcohols

The solid fatty alcohol may be crystalline, amorphous or pasty. The solid fatty alcohols are solid at room temperature (25 degrees centigrade) and at atmospheric pressure (1 atm) and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, chloroform, benzene or liquid petroleum jelly) to at least 1% by weight.

In some cases, the solid fatty alcohols preferably have a melting point of greater than or equal to 28° C. and have a viscosity, at a temperature of 40° C. and at a shear rate of 1 $s^{-1}$, of greater than or equal to 1 Pa·s. Moreover, the melting point of the fatty alcohols may ranges from 30° C. to 250° C., such as from 32° C. to 150° C. or such as from 35° C. to 150° C. The melting points may be measured by DSC or on a Kofler bench. The melting point may be measured by differential calorimetric analysis (DSC) with a temperature rise of 10° C. per minute. The melting point is then the temperature corresponding to the top of the melting endotherm peak obtained during the measurement.

The viscosity measurements may be taken at a temperature of about 40° C. using an RS600 rheometer from Thermoelectron.

The solid fatty alcohols of the present invention are chosen from saturated or unsaturated, linear or branched, preferably linear and saturated, (mono) alcohols comprising from 8 to 40 carbon atoms, such as from 10 to 30 carbon atoms, or such as from 12 to 24 carbon atoms.

The solid fatty alcohols preferably have the structure of formula: R—OH in which R especially denotes a C6-C60, for example, C8-C60, preferably C10-C50 or even C12-C30 alkyl group, R possibly being substituted with one or more hydroxyl groups, R possibly being branched.

In an embodiment, the solid fatty alcohols are chosen from myristyl alcohol, cetyl alcohol, stearyl alcohol and behenyl alcohol, and mixtures thereof.

Other suitable examples of the solid fatty alcohol of the present invention include branched solid fatty alcohols chosen from 2-dodecylhexadecanol, 2-tetradecyl-1-octadecanol, 2-tetradecyl-1-eicosanol, 2-hexadecyl-1-octadecanol and 2-hexadecyl-1-eicosanol, and mixtures thereof.

The solid fatty alcohol may represent a mixture of fatty alcohols, which means that several species of fatty alcohol may coexist, in the form of a mixture, in a commercial product.

The solid fatty alcohols of the invention are preferably non-oxyalkylenated and/or non-glycerolated. These fatty alcohols may be constituents of animal or plant waxes.

In an embodiment, the solid fatty alcohols are chosen from cetyl alcohol, stearyl alcohol and mixtures thereof (cetylstearyl alcohol or cetearyl alcohol).

Non-Silicone Shine Enhancers

The hair color toning compositions include one or more non-silicone shine enhancers, including at least one liquid fatty alcohol chosen from saturated or unsaturated, linear or branched alcohols comprising from 6 to 50 carbon atoms and preferably from 8 to 30 carbon atoms. The liquid fatty alcohol(s) are liquid at room temperature (25° C.) and at atmospheric pressure (1 atm) and are insoluble in water (i.e. they have a solubility in water of less than 1% by weight and preferably less than 0.5% by weight, at 25° C. and 1 atm) and are soluble, under the same temperature and pressure conditions, in at least one organic solvent (for example ethanol, chloroform, benzene or liquid petroleum jelly) to at least 1% by weight. Mention may be made, for example, of octyldodecanol, 2-butyloctanol, 2-hexyldecanol, 2-undecylpentadecanol, oleyl alcohol or linoleyl alcohol.

The saturated liquid fatty alcohols can be branched. They can optionally comprise, in their structure, at least one aromatic or non-aromatic ring. They can be acyclic. Among liquid saturated fatty alcohols, octyldodecanol, isostearyl alcohol and 2-hexyldecanol can be cited.

The unsaturated liquid fatty alcohols may exhibit in their structure, at least one double or triple bond and preferably one or more double bonds. When several double bonds are present, there are preferably 2 or 3 of them and they can be conjugated or unconjugated. These unsaturated fatty alcohols can be linear or branched. They can optionally comprise, in their structure, at least one aromatic or non-aromatic ring. They can be acyclic. Among the liquid unsaturated fatty alcohols, oleyl alcohol, linoleyl alcohol, linolenyl alcohol and undecylenyl alcohol may be mentioned.

Non-Ionic Surfactants

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol (C$_6$-C$_{24}$)alkylpolyglycosides; N-(C$_6$-C$_{24}$)alkylglucamine derivatives, amine oxides such as (C$_{10}$-C$_{14}$)alkylamine oxides or N-(C$_{10}$-C$_{14}$)acylaminopropylmorpholine oxides; and a mixture thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

Examples of oxyalkylenated nonionic surfactants that may be mentioned include: oxyalkylenated (C$_8$-C$_{24}$)alkylphenols, saturated or unsaturated, linear or branched, oxyalkylenated C$_8$-C$_{30}$ alcohols, saturated or unsaturated, linear or branched, oxyalkylenated C$_8$-C$_{30}$ amides, esters of saturated or unsaturated, linear or branched, C$_8$-C$_{30}$ acids and of polyethylene glycols, polyoxyalkylenated esters of saturated or unsaturated, linear or branched, C$_8$-C$_{30}$ acids and of sorbitol, saturated or unsaturated, oxyalkylenated plant oils, condensates of ethylene oxide and/or of propylene oxide, inter alia, alone or as mixtures.

The surfactants preferably contain a number of moles of ethylene oxide and/or of propylene oxide of between 2 and 100 and most preferably between 2 and 50.

In accordance with one preferred embodiment of the invention, the oxyalkylenated nonionic surfactants are chosen from oxyethylenated C$_8$-C$_{30}$ alcohols.

Examples of ethoxylated fatty alcohols (or C$_8$-C$_{30}$ alcohols) that may be mentioned include the adducts of ethylene oxide with lauryl alcohol, especially those containing from 9 to 50 oxyethylene groups and more particularly those containing from 10 to 25 oxyethylene groups (Laureth-10 to Laureth-25); the adducts of ethylene oxide with behenyl alcohol, especially those containing from 9 to 50 oxyethylene groups (Beheneth-9 to Beheneth-50); the adducts of ethylene oxide with cetearyl alcohol (mixture of cetyl alcohol and stearyl alcohol), especially those containing from 10 to 30 oxyethylene groups (Ceteareth-10 to Ceteareth-30); the adducts of ethylene oxide with cetyl alcohol, especially those containing from 10 to 30 oxyethylene groups (Ceteth-10 to Ceteth-30); the adducts of ethylene oxide with stearyl alcohol, especially those containing from 10 to 30 oxyethylene groups (Steareth-10 to Steareth-30); the adducts of ethylene oxide with isostearyl alcohol, especially those containing from 10 to 50 oxyethylene groups (Isosteareth-10 to Isosteareth-50); and a mixture thereof.

As examples of polyglycerolated nonionic surfactants, polyglycerolated C$_8$-C$_{40}$ alcohols are preferably used.

In particular, the polyglycerolated C$_8$-C$_{40}$ alcohols correspond to the following formulae:

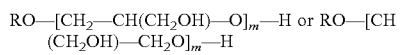

RO—[CH$_2$—CH(CH$_2$OH)—O]$_m$—H or RO—[CH(CH$_2$OH)—CH$_2$O]$_m$—H in which R represents a linear or branched C$_8$-C$_{40}$ and preferably C$_8$-C$_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a C$_8$-C$_{24}$, preferably C$_{12}$-C$_{22}$, fatty acid or acids and alkoxylated derivatives thereof, preferably with a number of alkyleneoxide of from 10 to 200, and more preferably from 10 to 100; polyethylene glycol esters of a C$_8$-C$_{24}$, preferably C$_{12}$-C$_{22}$, fatty acid or acids and alkoxylated derivatives thereof, preferably with a number of alkyleneoxide of from 10 to 200, and more preferably from 10 to 100; sorbitol esters of a C$_8$-C$_{24}$, preferably C$_{12}$-C$_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a C$_8$-C$_{24}$, preferably C$_{12}$-C$_{22}$, fatty acid or acids and alkoxylated derivatives thereof, preferably with a number of alkyleneoxide of from 10 to 200, and more preferably from 10 to 100; ethers of fatty alcohols; ethers of sugar and a C$_8$-C$_{24}$, preferably C$_{12}$-C$_{22}$, fatty alcohol or alcohols; and a mixture thereof.

Examples of ethoxylated fatty esters that may be mentioned include the adducts of ethylene oxide with esters of lauric acid, palmitic acid, stearic acid or behenic acid, and a mixture thereof, especially those containing from 9 to 100 oxyethylene groups, such as PEG-9 to PEG-50 laurate; PEG-9 to PEG-50 palmitate; PEG-9 to PEG-50 stearate; PEG-9 to PEG-50 palmitostearate; PEG-9 to PEG-50 behenate; polyethylene glycol 100 EO monostearate; and a mixture thereof.

As glyceryl esters of fatty acids, glyceryl stearate (glyceryl mono-, di- and/or tristearate) (glyceryl stearate) or glyceryl ricinoleate and a mixture thereof can in particular be cited.

As glyceryl esters of C$_8$-C$_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Croda, and a product containing glyceryl stearate (glyceryl mono- and distearate) and potassium stearate, can also be used.

The sorbitol esters of C$_8$-C$_{24}$ fatty acids and alkoxylated derivatives thereof can be selected from sorbitan palmitate, sorbitan trioleate and esters of fatty acids and alkoxylated sorbitan containing for example from 20 to 100 EO, such as for example polyethylene sorbitan trioleate (polysorbate 85) or the compounds marketed under the trade names Tween 20 or Tween 60 by Croda.

As esters of fatty acids and glucose or alkylglucose, in particular glucose palmitate, alkylglucose sesquistearates such as methylglucose sesquistearate, alkylglucose palmitates such as methylglucose or ethylglucose palmitate, methylglucoside fatty esters and more specifically the diester of methylglucoside and oleic acid (Methyl glucose dioleate), the mixed ester of methylglucoside and the mixture oleic acid/hydroxystearic acid (Methyl glucose dioleate/hydroxystearate), the ester of methylglucoside and isostearic acid (Methyl glucose isostearate), the ester of methylglucoside and lauric acid (Methyl glucose laurate), the mixture of monoester and diester of methylglucoside and isostearic acid (Methyl glucose sesqui-isostearate), the mixture of monoester and diester of methylglucoside and stearic acid (Methyl glucose sesquistearate) and in particular the product marketed under the name Glucate SS by Lubrizol, and a mixture thereof can be cited.

As ethoxylated ethers of fatty acids and glucose or alkylglucose, ethoxylated ethers of fatty acids and methylglucose, and in particular the polyethylene glycol ether of the diester of methylglucoside and stearic acid with about 20 moles of ethylene oxide (PEG-20 methyl glucose distearate) such as the product marketed under the name GLUCAM E-20 DISTEARATE by Lubrizol, the polyethylene glycol ether of the mixture of monoester and diester of methylglucose and stearic acid with about 20 moles of ethylene oxide (PEG-20 methyl glucose sesquistearate) and in particular the product marketed under the name GLUCAMATE SSE-20 by Lubrizol, and a mixture thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLATAREN 2000 by BASF, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by BASF, coco-glucoside such as the product marketed under the name PLANTACARE 818/UP by BASF, cetostearyl glucoside possibly mixed with cetostearyl alcohol, marketed for example under the name MONTANOV 68 by Seppic, under the name TEGO-CARE CG90 by Evonik, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and a mixture thereof can in particular be cited.

Mixtures of glycerides of alkoxylated plant oils such as mixtures of ethoxylated (200 EO) palm and copra (7 EO) glycerides can also be cited.

It is preferable that the nonionic surfactant be selected from the group consisting of PEG-7 glyceryl cocoate, PEG-20 methylglucoside sesquistearate, PEG-20 glyceryl tri-isostearate, PG-5 dioleate, PG-4 diisostearate, PG-10 isostearate, PEG-8 isostearate, and PEG-60 hydrogenated castor oil.

Mixtures of these oxyethylenated derivatives of fatty alcohols and of fatty esters may also be used.

Preferably, the nonionic surfactant may be a nonionic surfactant with an HLB of 18.0 or less, such as from 4.0 to 18.0, more preferably from 6.0 to 15.0 and furthermore preferably from 9.0 to 13.0. The HLB is the ratio between the hydrophilic part and the lipophilic part in the molecule.

In some case, the nonionic surfactant is a fatty alkanol-amide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

Amidoamines

In some cases, useful amidoamine compounds are those corresponding to the following formula and their salts:

wherein R is a hydrocarbon radical containing at least 6 carbon atoms: R' is a divalent hydrocarbon radical containing less than 6 carbon atoms; and R" is H or a hydrocarbon radical containing less than 6 carbon atoms. In addition, R can be linear or branched, acyclic or cyclic, saturated or unsaturated, aliphatic or aromatic, substituted or unsubstituted, and R" can be linear or branched, acyclic or cyclic, saturated or unsaturated, substituted or unsubstituted. Typically, R is a linear or branched, acyclic alkyl or alkenyl group or an alkyl phenyl group, R' is a divalent hydrocarbon radical containing 2 or 3 carbon atoms, and R" is a linear or branched, acyclic alkyl or alkenyl group. In some cases, R" is H or a methyl group.

Examples of amidoamines that are useful in the compositions of the instant disclosure include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicamidopropyl dimethylamine, olivamidopropyl dimethylamine, palmitamidopropyl dimethylamine, stearamidoethyldiethylamine, and mixtures thereof.

Acids

The at least one acid may be chosen from organic acids such as monocarboxylic acids and polycarboxylic acids (with 2 or more carboxylic acid groups).

Suitable examples of the organic acid include acetic acid, terephthalic acid, HOOC-PEG-COOH acid; citric acid, tartaric acid; betaine hydrochloride, gluconic acid or 2-ethylcaproic acid, lactic acid, salicylic acid, glycolic acid, malic acid, oxalic acid, malonic acid, aspartic acid, glutamic acid, benzoic acid, acetic acid, formic acid, and mixtures thereof.

Other suitable examples of the at least organic acid are chosen from polycarboxylic acids selected from aspartic acid, glutamic acid, oxalic acid, succinic acid, tartaric acid, mucic acid, citric acid, malic acid, phthalic acid, poly (ethylene glycol) bis(carboxymethyl)ethers, acrylic polyacid, copolymer of acrylic acid and maleic acid, polyaspartic acid, and carboxylic polydimethylsiloxanes.

In other embodiments, the organic acid is a sulfonic acid selected from benzene sulfonic acid, sulfonic acid HSO2OH, taurine, 2-[4-(2-hydroxy-ethyl)-piperazin-1-yl] ethane sulfonic acid (or HEPES), and (3E)-3-(4-{(E)-[7,7-dimethyl-3-oxo-4-(sulfomethyl)bicyclo[2.2.1]hept-2-ylidene]methyl}benzylidene)-7,7-dimethyl-2-oxobicyclo [2.2.1]hept-1-yl]methane sulfonic acid.

In an embodiment, the organic acid is selected from trichloroacetic acid, L-glutamic acid, lactic acid, succinic acid, tartaric acid, poly(ethylene glycol) bis(carboxymethyl) ether having a molecular weight of 250 g/mol, salicylic acid derivatives, jasmonic acid derivative, 3-hydroxy-2-pentyl-cyclopentyl acetic acid, 2-[4-(2-hydroxy-ethyl)-piperazin-1-yl]-ethanesulfonic acid, malic acid, pyruvic acid, and mandelic acid.

In an embodiment, the organic acid is selected from tartaric acid, lactic acid, malic acid, oxalic acid, malonic acid, citric acid, aspartic acid, glutamic acid, salicylic acid, benzoic acid, acetic acid, formic acid and mixtures thereof.

The total amount of acids may, in various embodiments, be present in amount sufficient to neutralize the one or more amidoamines and/or to achieve a desired pH. For example, the total amount of acids may range from about 0.01 to about 5%, such as about 0.01 to about 4%, about 0.01 to about 3%, about 0.01 to about 2%, about 0.05 to about 5%, about 0.05 to about 4%, about 0.05 to about 3%, about 0.05 to about 2%, about 0.1 to about 5%, about 0.1 to about 4%, about 0.1 to about 3%, about 0.1 to about 2% or about 0.1 to about 1%, based on the total weight of the hair color toning composition.

Direct Dyes

Compositions according to embodiments of the disclosure comprise at least one direct dye. Direct dyes may be synthetic or natural direct dyes, for example, chosen from anionic, cationic, and nonionic species, as well as mixtures thereof.

Examples of suitable direct dyes that may be mentioned include azo direct dyes; (poly)methine dyes such as cyanins, hemicyanins and styryls; carbonyl dyes; azine dyes; nitro (hetero)aryl dyes; tri(hetero)arylmethane dyes; porphyrin dyes; phthalocyanin dyes, and natural direct dyes, alone or as mixtures.

Non-limiting examples of direct dyes include nitro dyes which may be chosen from HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Nitro dyes include non-ionic direct dyes that are typically hydrophobic. Non-limiting examples of hydrophobic direct dyes may be chosen from HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15.

In an embodiment, the hydrophobic direct dyes of the present disclosure are chosen from HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue 15, HC Blue No. 17, and mixtures thereof.

Direct dyes may also be chosen from cationic direct dyes. Mention may be made of the hydrazono cationic dyes of formulas (Va) and (V'a), the azo cationic dyes (VIa) and (VI'a) and the diazo cationic dyes (VIIa) below:

| | |
|---|---|
| Het$^+$-C(R$^a$)=N—N(R$^b$)—Ar, An$^-$ | (Va) |
| Het$^+$-N(R$^a$)—N=C(R$^b$)—Ar, An$^-$ | (V'a) |
| Het$^+$-N=N—Ar, An$^-$ | (VIa) |
| Ar$^+$-N=N—Ar'', An$^-$ | (VI'a) and |
| Het$^+$-N=N—Ar'—N=N-Ar, An$^-$ | (VIIa) | in which formulas (Va (V'a), (VIa), (VI'a) and (VIIa):

Het$^+$ represents a cationic heteroaryl radical, preferably bearing an endocyclic cationic charge, such as imidazolium, indolium or pyridinium, optionally substituted preferentially with one or more ($C_1$-$C_8$) alkyl groups such as methyl;

Ar$^+$ representing an aryl radical, such as phenyl or naphthyl, bearing an exocyclic cationic charge, preferentially ammonium, particularly tri($C_1$-$C_8$)alkylammonium such as trimethylammonium;

Ar represents an aryl group, especially phenyl, which is optionally substituted, preferentially with one or more electron-donating groups such as i) optionally substituted ($C_1$-$C_8$)alkyl, ii) optionally substituted ($C_1$-$C_8$) alkoxy, iii) (di)($C_1$-$C_8$)(alkyl)amino optionally substituted on the alkyl group(s) with a hydroxyl group, iv) aryl($C_1$-$C_8$)alkylamino, v) optionally substituted N-($C_1$-$C_8$)alkyl-N-aryl($C_1$-$C_8$)alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups ($C_1$-$C_8$)alkyl, hydroxyl or ($C_1$-$C_8$)alkoxy;

Ar'' is an optionally substituted (hetero)aryl group such as phenyl or pyrazolyl, which are optionally substituted, preferentially with one or more groups ($C_1$-$C_8$)alkyl, hydroxyl, (di)($C_1$-$C_8$)(alkyl)amino, ($C_1$-$C_8$)alkoxy or phenyl;

$R^a$ and $R^b$, which may be identical or different, represent a hydrogen atom or a group ($C_1$-$C_8$)alkyl, which is optionally substituted, preferentially with a hydroxyl group;

or alternatively the substituent $R^a$ with a substituent of Het$^+$ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group ($C_1$-$C_4$)alkyl, which is optionally substituted with a hydroxyl group; and An$^-$ represents an anionic counter-ion such as mesylate or halide.

In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

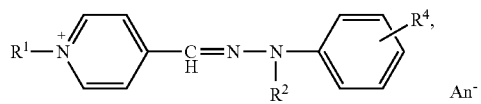

(Va-1)

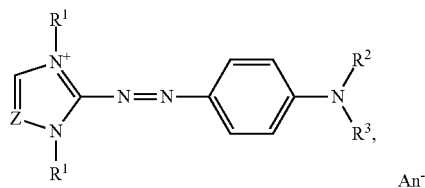

(VIa-1)

wherein in formulae (Va-1) and (VIa-1):

$R^1$ representing a ($C_1$-$C_4$) alkyl group such as methyl;

$R^2$ and $R^3$, which are identical or different, represent a hydrogen atom or a ($C_1$-$C_4$)alkyl group, such as methyl;

$R^4$ represents a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group(s) with a hydroxyl group; particularly, $R^4$ is a hydrogen atom;

Z represents a CH group or a nitrogen atom, preferentially CH; and

An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

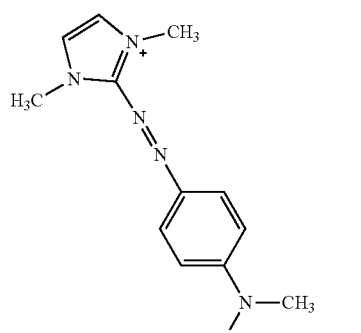

Basic Red 51

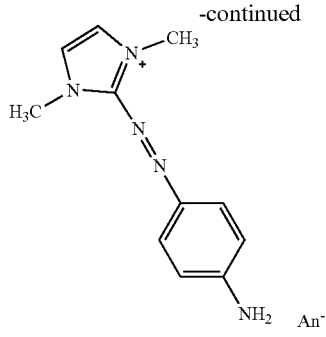

Basic Orange 31

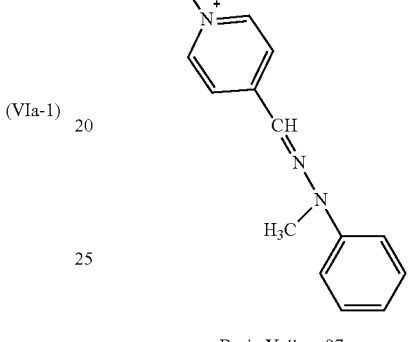

Basic Yellow 87

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic direct dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Among the natural direct dyes, mention may be made of lawsone, juglone, alizarin, purpurin, carminic acid, kermesic acid, purpurogallin, protocatechaldehyde, indigo, isatin, curcumin, spinulosin, apigenidin and orceins. Extracts or decoctions containing these natural dyes and in particular henna-based poultices or extracts may also be used.

In one embodiment, the compositions are free or substantially free of cationic anthraquinone dyes. In a further embodiment, the compositions are free or substantially free of HC Blue16. In yet a further embodiment, the compositions are free or substantially free of hydroxyanthroauinone aminopropyl morpholinium methosulfate.

The direct dyes are present in the hair color toning compositions in an amount sufficient to refresh the color of, or impart tone to, the hair. For example, the compositions may comprise one or more direct dyes, where the total amount of direct dyes ranges from about 0.001% to 10% by weight, such as from about 0.005% to 8% by weight, or from about 0.01% to 6% by weight, or from about 0.01% to about 5% by weight, or from about 0.02% to about 4% by weight, or from about 0.03% to about 3% by weight, or from about 0.03% to about 3.5% by weight, or from about 0.04% to about 3% by weight, or from about 0.04% to 2.5% by weight, or from about 0.05% to 2% by weight, or from about 0.05% to 1.5% by weight, or from about 0.01% to about 3% by weight, or from about 0.02% to about 2.5% by weight, or from about 0.03% to about 2% by weight, or from about 0.04% to about 1.5% by weight, or from about 0.05% to about 1% by weight, or from about 0.05% to about 0.8% by weight, of the total weight of the composition of the present disclosure.

In preferred embodiments, the hair color toning compositions comprise a combination of HC Violet 2 and Basic Red 51; a combination of Basic Red 51 and Basic Yellow 87; a combination of HC Violet 2, 2-nitro-5-glyceryl methylaniline, and 3-methylamino-4-nitrophenoxyethanol; a combination of HC Violet 2, 2-nitro-5-glyceryl methylaniline, and 3-methylamino-4-nitrophenoxyethanol, optionally with Basic Yellow 87 and/or Basic Orange 31; a combination of HC Violet 2, HC Blue 2, and 2-nitro-5-glyceryl methylaniline; a combination of HC Violet 2, HC Blue 2, 2-nitro-5-glyceryl methylaniline, and Basic Yellow 57; a combination of HC Blue No. 15, 2-nitro-5-glyceryl methylaniline, HC Blue 2, and External Violet 2; or a combination of HC Blue No. 15, Basic Yellow 87, and Basic Yellow 57, with the understanding that the total amount of the aforementioned dyes in any of the recited combinations ranges from about 0.001% to about 5%, such as about 0.01% to about 3%, about 0.05% to about 2%, or about 0.05% to 1% by weight, relative to the total weight of the hair color toning composition.

Cosmetically Acceptable Carrier

In addition to water, the cosmetically acceptable carrier may optionally include, for example, glycerin, $C_{1-4}$ alcohols, organic solvents, fatty alcohols, fatty ethers, fatty esters, polyols, glycols, mineral oils, liposomes, laminar lipid materials, or any combinations thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

In some instances, cosmetically acceptable carriers may comprise water, a mixture of water and at least one cosmetically acceptable organic solvent, or at least one cosmetically acceptable organic solvent. Additionally, cosmetically acceptable carriers may be or may include ethanol, a glycol ether, for example, dipropylene glycol n-butyl ether, isododecane, mineral oil, propylene glycol, pentylene glycol, hexylene glycol, glycerol, and mixtures thereof.

Thickening Agents

The hair color toning compositions may optionally contain one or more thickeners or viscosity modifying agents. Classes of such agents include, but are not limited to, semisynthetic polymers, such as semisynthetic cellulose derivatives, synthetic polymers, such as carbomers, poloxamers, and polyethyleneimines (e.g., PEI-10), naturally occurring polymers, such as acacia, tragacanth, alginates (e.g., sodium alginate), carrageenan, vegetable gums, such as xanthan gum, petroleum jelly, waxes, particulate associate colloids, such as bentonite, colloidal silicon dioxide, and microcrystalline cellulose, surfactants, such as PPG-2 hydroxyethyl coco/isostearamide, emulsifiers, such as disteareth-75 IPDI, and salts, such as sodium chloride, and combinations thereof. Natural thickening agent agents are preferred.

The total amount of the one or more thickening agents may vary, but in some cases is about 0.1 to about 15%, about 0.1 to about 10%, about 0.1 to about 8%, about 0.1 to about 6%, about 0.1 to about 5%, about 0.5 to about 10%, about 0.5 to about 8%, about 0.5 to about %, about 0.5 to about 5%, about 1 to about 10%, about 1 to about 8%, about 1 to about 6%, or about 1 to about 5% by weight, based on the total weight of the composition.

Preservatives

One or more preservatives may optionally be included in the hair color toning compositions described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediamine-tetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5%, about 0.01 to about 4%, about 0.15 to about 1%, or about 0.2 to about 3% by weight, based on the total weight of the composition.

Additional Components

The composition according to the disclosure may optionally comprise any auxiliary or additional component suitable for use in cosmetic compositions, and in particular suitable for hair color toning compositions. Such components may include, but are not limited to, dyes/pigments other than those listed above, silicone compounds, rheology modifying agents such as acrylic polymers, cationic, nonionic, amphoteric or zwitterionic surfactants or mixtures thereof, anionic, cationic, nonionic, amphoteric or zwitterionic polymers or mixtures, film forming agents or polymers, humectants and moisturizing agents, fatty substances other than those described above, emulsifying agents, fillers, structuring agents, propellants, shine agents other than those listed above, antioxidants or reducing agents, penetrants, sequestrants, fragrances, buffers, dispersants, conditioning agents (e.g. plant extracts), ceramides, opacifiers, sunscreen agents, and antistatic agents.

Methods

The compositions according to the disclosure can impart improved properties to the hair, such as improved strength, shine, conditioning, feel, detangling, and/or combability, while also imparting excellent color and/or tone and/or anti-brassiness color effects to the hair. Therefore, another aspect of the invention pertains to methods of using any of the compositions described herein by applying the compositions to the hair.

In one embodiment, the invention is directed to imparting color or tone to hair using short processing times such as about 20 minutes or less, or about 15 minutes or less, or about 10 minutes or less, or about 5 minutes or less, or about 3 minutes or less, for example about 3 minutes to about 15 minutes, or about 5 minutes to about 10 minutes. In various embodiments, the invention is directed to imparting color or tone to hair using processing times such as about 20 minutes, about 15 minutes, about 14 minutes, about 13 minutes, about 12 minutes, about 11 minutes, about 10 minutes, about 9 minutes, about 8 minutes, about 7 minutes, about 6 minutes, about 5 minutes, about 4 minutes, or about 3 minutes or less.

In one embodiment, the method comprises applying the hair color toning compositions directly to hair. The hair color toning composition may be left on the hair for a period of time sufficient to achieve the desired effect. For example, the hair composition may be left on the hair for up to one hour, such as from about 3 minutes to about 45 minutes, from about 5 minutes to about 30 minutes, or from about 5 minutes to about 10 minutes. One skilled in the art will be able to determine an appropriate amount of time to leave the hair color toning composition on the hair in order to achieve the desired effect. If desired, the composition may, optionally, be shampooed and/or rinsed off the hair.

Kits

Another aspect of the disclosure pertains to kits which comprise any of the hair color toning compositions described herein for use in exemplary methods according to the disclosure. In some embodiments, the kit comprises a hair color toning composition according to the disclosure and optionally, a shampoo and/or a conditioner and/or a masque treatment. The compositions may be contained in different compartments or containers.

In various embodiments, the kits may contain a device, e.g. a bottle, tube, etc., for applying the hair color toning compositions according to the disclosure. Exemplary and non-limiting applicator devices include bottles, tubes, etc., that are plastic, aluminum, etc., and may be squeezed by the user to expel the hair color toning composition through an opening or passage. Exemplary applicator devices may comprise various configurations of openings or passages through which the composition may be expelled, for example a nozzle, a screw top, a flip top, etc. It will be understood by those skilled in the art that the passage is preferably configured so that the appropriate amount of hair color altering composition is expelled during use, for example that the passage is of the appropriate dimensions to control the amount of composition expelled. By way of non-limiting example only, a useful applicator may comprise a plastic squeeze-type bottle having a nozzle-type tip with a substantially circular opening, where the tip has a sufficient diameter in the opening to control the amount of hair color toning composition that passes through such that it is not too much nor too little to effectively apply the composition to the hair during use. Such exemplary and non-limiting openings may have diameters ranging from about 0.05 mm to about 0.15 mm, such as about 0.08 mm to about 0.13 mm, or about 0.1 mm to about 0.15 mm. In various embodiments, such diameters may be particularly suitable for application of the hair color toning compositions described herein. In a further non-limiting example only, a useful applicator may comprise a bottle or tube that is deformable when squeezed, and that has a tip with a substantially rectangular or oval opening, where the tip has a sufficient width in the opening to control the amount of hair color toning composition that passes through such that it is not too much nor too little to effectively apply the composition to the hair during use Suitable components, such as those listed in the instant disclosure (including those listed above), may be included or excluded from the hair color toning formulations depending on the specific combination of other components, the form of the compositions, and/or the use of the formulation. In various embodiments, the hair color toning compositions according to the instant disclosure can be in the form of a hair spray, lotion (e.g., a milky lotion), light serum, light cream, conditioner, or non-aerosolized hair spray (for example, packaged as a pump spray or squeeze-bottle spray).

According to at least one embodiment, the kits comprising the hair color toning compositions according to the disclosure are free or substantially free of alkalizing agents, oxidation dyes, couplers, and/or developer compositions.

As used herein, the terms "comprising," "having," and "including" (or "comprise," "have," and "include") are used in their open, non-limiting sense.

The terms "a," "an," and "the" are understood to encompass the plural as well as the singular.

Thus, the term "a mixture thereof" or "a combination thereof" also relates to "mixtures thereof" and "combinations thereof." Throughout the disclosure, the terms "a mixture thereof" and "a combination thereof" is used, following a list of elements as shown in the following example where letters A-F represent the elements: "one or more elements selected from the group consisting of A, B, C, D, E, F, and a mixture thereof." The terms "a mixture thereof" or "a combination thereof" not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts which are referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

"Conditioning" as used herein means imparting to one or more hair fibers at least one property chosen from combability, moisture-retentivity, luster, shine, and/or softness. The state of conditioning can be evaluated by any means known in the art, such as, for example, measuring, and comparing, the ease of combability of the treated hair and of the untreated hair in terms of combing work, and consumer perception.

The term "treat" (and its grammatical variations) as used herein refers to the application of the compositions of the present disclosure onto the surface of hair. The term "treat" (and its grammatical variations) as used herein also refers to contacting hair with the compositions of the present disclosure.

As used herein, "color-refreshing" means depositing color onto the hair, typically hair that has previously been bleached and/or color-treated, in order to change the color of the hair, to refresh or liven up color that has become dull, e.g. in between hair color treatments, etc. As used herein, "toning" can refer to neutralizing underlying colors of bleached and/or color-treated hair in order to achieve a more natural look (for example, green color or shade neutralizes red, blue color or shade neutralizes orange, purple/violet color or shade neutralizes yellow). Neutralizing underlying colors can also refer to removing the brassiness of artificial color on hair. It should be understood that hair color-refreshing and hair color toning are referred to interchangeably herein, and may be referred to collectively by the term "hair color toning composition" which is for ease of reference only and is not intended to limit the composition to "color-refreshing" or "color toning" unless expressly otherwise noted.

A "rinse off" product refers to a composition such as a hair color toning composition that is rinsed and/or washed with water either after or during the application of the composition onto the keratinous substrate, and before drying and/or styling said keratinous substrate. At least a portion, and typically most, of the composition is removed from the keratinous substrate during the rinsing and/or washing.

The term "stable" as used herein means that the composition does not exhibit phase separation and/or crystallization for a period of time, for example, for at least 1 day (24 hours), one week, one month, or two months.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

The term "substantially free" or "essentially free" as used herein means that there is less than about 5% by weight of a specific material added to a composition, based on the total weight of the compositions. Nonetheless, the compositions may include less than about 3%, less than about 2%, less than about 1%, less than about 0.5%, less than about 0.1% less than about 0.01%, or none of the specified material.

All ranges and values disclosed herein are inclusive and combinable. For examples, any value or point described herein that falls within a range described herein can serve as a minimum or maximum value to derive a sub-range, etc.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The following examples serve to illustrate embodiments of the present disclosure without, however, being limiting in nature. It will be apparent to those skilled in the art that various modifications and variations can be made in the delivery system, composition and methods of the invention without departing from the spirit or scope of the invention. Thus, it is intended that the present disclosure cover the modifications and variations that come within the scope of the appended claims and their equivalents.

EXAMPLES

Implementation of the present disclosure is demonstrated by way of the following non-limiting examples.

Example 1

Inventive Formulations

Hair color toning/refresher compositions 1A-1K according to the disclosure were prepared as follows. The direct dyes were added to water at a temperature of about 70° C., with agitation until the dyes were fully solubilized. All remaining components were added except the vegetable oils and extracts, and any fragrance, with homogenization. Once the mixture was homogenous, additional water was added and the mixture was cooled. The vegetable oils and extracts and fragrance were added to the mixture at a temperature of about 45° C., and the mixture cooled to room temperature.

TABLE 1-1

Hair Color Refresher Formulations
The following formulations, which are hair color refreshers, were prepared.

| INCI NAME | Inventive Formulations | | | | | | | |
| --- | --- | --- | --- | --- | --- | --- | --- | --- |
| | 1A | 1B | 1E | 1F | 1G | 1H | 1I | 1K |
| BRASSICAMIDO-PROPYL DIMETHYLAMINE | 2.5000 | 2.5000 | 2.5000 | 2.5000 | 2.5000 | 2.5000 | 2.5000 | 2.5000 |
| CETEARYL ALCOHOL | 3.0000 | 3.0000 | 3.0000 | 3.0000 | 3.0000 | 3.0000 | 3.0000 | 3.0000 |
| GLYCERYL STEARATE | 0.1500 | 0.1500 | 0.1500 | 0.1500 | 0.1500 | 0.1500 | 0.1500 | 0.1500 |

TABLE 1-1-continued

Hair Color Refresher Formulations
The following formulations, which are hair color refreshers, were prepared.

| INCI NAME | Inventive Formulations | | | | | | | |
|---|---|---|---|---|---|---|---|---|
| | 1A | 1B | 1E | 1F | 1G | 1H | 1I | 1K |
| TARTARIC ACID and/or CITRIC ACID | 0.3501 | 0.3601 | 0.3501 | 0.3505 | 0.3501 | 0.3501 | 0.3501 | 0.3505 |
| COCOS NUCIFERA (COCONUT) OIL and/or CAMELLIA OLEIFERA SEED OIL | 1.1000 | 1.1000 | 1.1000 | 1.1000 | 1.1000 | 1.1000 | 1.1000 | 1.1000 |
| OCTYL-DODECANOL | 0.5000 | 0.5000 | 0.5000 | 0.5000 | 0.5000 | 0.5000 | 0.5000 | 0.5000 |
| HC VIOLET NO. 2 | 0.1000 | | | | | | | 0.0098 |
| HC BLUE NO. 2 | | 0.0630 | | 0.0860 | 0.0860 | 0.0500 | | |
| BASIC YELLOW 87 | | | | 0.2000 | 0.2000 | | 0.1200 | 0.0084 |
| BASIC YELLOW 57 | | | 0.0480 | | | | | |
| EXT. VIOLET 2 | | 0.1000 | | | | | | |
| BASIC BROWN 17 | | | 0.0090 | | | 0.3000 | | |
| HC BLUE NO. 15 | | 0.0013 | | | | | | |
| BASIC RED 51 | 0.0007 | | | | | 0.0087 | 0.1176 | 0.0004 |
| 2-NITRO-5-GLYCERYL METHYLANILINE | | 0.0038 | | 0.0430 | 0.0430 | 0.2500 | | |
| BASIC ORANGE 31 | | | | 0.2000 | 0.2000 | | | |
| 3-METHYLAMINO-4-NITROPHEN-OXYETHANOL | | | | | | 0.0500 | | |
| XANTHAN GUM | 0.0001 | 0.0001 | 0.0001 | 0.0005 | 0.0001 | 0.0001 | 0.0001 | 0.0001 |
| ONE OR MORE OF PLANT/VEGETABLE EXTRACTS, FRAGRANCES, pH ADJUSTERS, VITAMINS, PRESERVATIVES, CHELANTS, SALT (SODIUM CHLORIDE), and/or UV FILTERS | ≤2.00 | ≤2.00 | ≤2.00 | ≤2.00 | ≤2.00 | ≤2.00 | ≤2.00 | ≤2.00 |
| WATER and/or BUTYLENE GLYCOL and/or CAPRYLYL GLYCOL | Q.S. | Q.S. | Q.S. | Q.S. | Q.S. | Q.S. | Q.S. | Q.S. |

TABLE 1-2

Hair Color Toner Formulations
The following formulations, which are hair color toners, were prepared.

| INCI NAME | Inventive Formulations | | |
|---|---|---|---|
| | 1C | 1D | 1J |
| BRASSICAMIDOPROPYL DIMETHYLAMINE | 2.5000 | 2.5000 | 2.5000 |
| CETEARYL ALCOHOL | 3.0000 | 3.0000 | 3.0000 |
| GLYCERYL STEARATE | 0.1500 | 0.1500 | 0.1500 |
| TARTARIC ACID and/or CITRIC ACID | 0.4901 | 0.3505 | 0.3500 |
| COCOS NUCIFERA (COCONUT) OIL and/or CAMELLIA OLEIFERA SEED OIL and/or GLYCINE SOJA (SOYBEAN) OIL | 1.1000 | 1.1000 | 1.1000 |
| OCTYLDODECANOL | 0.5000 | 0.5000 | 0.5000 |
| HC BLUE NO. 2 | 0.6000 | | 0.0450 |
| BASIC YELLOW 87 | 0.1000 | 0.0200 | |
| BASIC YELLOW 57 | | 0.1700 | |
| EXT, VIOLET 2 | 0.0150 | 0.0800 | 0.06 |
| HCBLUE NO. 15 | | | 0.0009 |
| 2-NITRO-5-GLYCERYL METHYLANILINE | | | 0.00277 |
| XANTHAN GUM | 0.0001 | 0.0005 | 0.0007 |
| ONE OR MORE OF PLANT/VEGETABLE EXTRACTS, FRAGRANCE, pH ADJUSTERS, VITAMINS, PRESERVATIVES, CHELANTS, and/or UV FILTERS | ≤2.0000 | ≤2.0000 | ≤2.0000 |

TABLE 1-2-continued

Hair Color Toner Formulations

The following formulations, which are hair color toners, were prepared.

| INCI NAME | Inventive Formulations | | |
|---|---|---|---|
| | 1C | 1D | 1J |
| WATER and/or GLYCERIN and/or BUTYLENE GLYCOL and/or CAPRYLYL GLYCOL | Q.S. | Q.S. | Q.S. |

The viscosities of formulations 1A-1K were found to be greater than about 12 DU (about 22 mPa·s) at 25° C., 200 RPM, 30 sec using a spindle #2 (Rheomat 180). The formulations all had fluid viscosities and milky appearances.

Each of formulations 1A-1K was stable for 2 months at room temperature, as well as at decreased and elevated temperatures. Each formulation was assessed at 1 week (4° C., 25° C., 45° C.), 1 month (4° C., 25° C., 45° C.), and 2 months (4° C., 25° C., 37° C., 45° C.) by visual inspection, by application to a swatch of hair, and by evaluating odor, pH, and viscosity.

Example 2

Evaluation of Inventive Formulations

Inventive hair color-refresher formulations 1A and 1B (Table 1-1) were each evaluated by 33 panelists (66 total panelists).

The panelists washed their previously color-treated hair with standard shampoo, squeezed excess water from their hair, applied the inventive formulation, waited for a period of about 5-10 minutes, rinsed their hair, and then dried and/or styled their hair as usual. The panelists reported the following results after the initial use.

TABLE 2-1

| Initial Results | |
|---|---|
| | Median (n = 66)* |
| Product is easy to apply | 8.5 |
| Product spreads evenly through hair | 8.0 |

TABLE 2-1-continued

| Initial Results | |
|---|---|
| | Median (n = 66)* |
| Product application is easy to control | 8.0 |
| Hair is easy to detangle | 8.0 |
| Hair feels soft | 8.0 |
| Hair feels silky smooth | 8.0 |
| Hair feels nourished/conditioned | 8.0 |
| Hair looks shiny/glossy | 7.0 |
| Hair looks silky smooth | 7.0 |
| Hair looks nourished/conditioned | 7.0 |
| Hair color looks vibrant/bright | 7.0 |
| Hair color looks refreshed | 7.0 |

*Scale of 1-9, where 1 = most negative; 9 = most positive

After 8 washes, the panelists evaluated the persistence of the initial results. The panelists reported the following results after 8 washes.

TABLE 2-2

| Results After 8 Washes | |
|---|---|
| | Median (n = 66)* |
| Hair color looks vibrant/bright | 7.0 |
| Hair color looks natural | 7.0 |
| Hair color does NOT look brassy | 8.0 |

*Scale of 1-9, where 1 = most negative; 9 = most positive

Overall, the panelists reported satisfaction with the performance of the product (either formulation 1A or 1B) immediately after use, after 8 washes, and after 4 weeks.

This Example demonstrates that the inventive compositions provide effective hair color benefits, while simultaneously providing cosmetic and sensorial advantages to the treated hair.

Example 3

Comparison with Commercial Hair Color Toning Formulations

The following commercial hair color toning formulation was obtained.

TABLE 3

| Commercial Hair Color Toning Formulation | |
|---|---|
| Example | Ingredient List from Package |
| 3A | Aqua, Amodimethicone, C11-15 Pareth-7, Laureth-9, Glycerin, Trideceth-12, Dicetyldimonium Chloride, Cetearyl Alcohol, Behentrimonium Methosulfate, Stearamidopropyl Di methylamine, Bis-Cetearyl Amodimethicone, Ceteareth-7, Ceteareth-25, Commiphora Myrrha Resin Extract, Propolis Extract, Beeswax, Candelilla Cera, PEG- 40, PPG-8, Methylaminopropyl, Hydropropyl Dimethicone Copolymer, Parfum, Glutamic Acid, Serine, Carbocysteine, Hydrolyzed Rice Protein, PEG-90M, Polyquaternium-10, Methylchloroisothiazolinone, Methyl isothiazolin one, Gossypium Herbaceum Seed Oil, Prunus Amygdalus Dulcis Oil, Zea Mays Oil, Helianthus Annuus Seed Oil, Triticum Volga re Germ Oil, Persea Gratissima Oil, Lecithin, Hydrogenated Polyisobuteno, Glyceryl Linoleate, Glyceryl Linolenate, Tocopheryl Acetate, Octyl dodecanol, Oleth-3, Acid Violet 43, Citric Acid, Arginine HCL, Acetyl Cysteine, Creatine, Proline, Glycine, Propylene Glycol, Panthenol, Keratin, Phenoxyethanol, Ethyl para ben, Methylparaben, Propylparaben, Butyl paraben, HC Blue 2 and Linalool |

In a half-head study, inventive hair color toning formulation 1J (Table 1-2) and commercial formulation 3A were applied to opposite sides of a head of bleached hair of a volunteer, and left on the hair of the designated side of the head for about 5 minutes. The compositions were then rinsed from the hair, which was then blow dried and styled.

The dried hair was evaluated for both color and care effects. The side of the head that was treated with inventive formulation 1J showed better hair color toning effects (cooler color, less brassy) than the side of the head that was treated with commercial formulation 3A (warmer color, more brassy). In addition, hair treated with inventive formulation 1J felt smoother, was easier to dry, and had better sealed ends, whereas the hair treated with commercial formulation 3A was more difficult to blow dry, felt rougher, appeared more dry with less sealed ends, and had more frizz and flyaways.

This Example demonstrates that the inventive formulations provide improved hair color toning and care effects relative to known commercial formulations.

Example 4

Comparative Hair Color Formulations

The following comparative hair color formulations were prepared.

TABLE 4

Comparative Hair Color Formulations

| INCI NAME | Comparative Formulations | | |
|---|---|---|---|
| | 4A | 4B | 4C |
| PEG-50 HYDROGENATED PALMAMIDE | | | 3.0000 |
| HYDROXYETHYL OLEYL DIMONIUM CHLORIDE | 1.4100 | | |
| PEG-2 OLEAMINE | | 0.1000 | |
| AMINOMETHYL PROPANOL | | 0.5000 | |
| LAURIC ACID | | 1.0000 | |
| POLYQUATERNIUM-11 | | 0.4000 | |
| GLYCOL DISTEARATE | 1.0000 | | |
| DECETH-5 | | | 1.8000 |
| LAURETH-12 | 9.3500 | | |
| HC RED NO. 3 | 0.0300 | | 0.0220 |
| HC BLUE NO. 2 | | | 0.7000 |
| GREEN 5 | | 0.0006 | |
| EXT. VIOLET 2 | | 0.0100 | |
| DISPERSE VIOLET 1 | | | 0.0420 |
| BASIC YELLOW 57 | 0.1000 | | |
| BASIC BROWN 17 | | | 0.1000 |
| HC BLUE NO. 14 | | | 0.0600 |
| 2-NITRO-5-GLYCERYL METHYLANILINE | | | 0.2700 |
| 3-METHYLAMINO-4-NITROPHENOXYETHANOL | 0.0300 | | 0.1000 |
| 4-AMINO-3-NITROPHENOL | 0.1130 | | |
| CELLULOSE GUM | 1.2000 | | |
| HYDROXYETHYLCELLULOSE | | | 1.2000 |
| HYDROXYETHYL CARBOXYMETHYL COCAM IDOPROPYLAMINE | 3.4527 | | |
| SODIUM LIGNOSULFONATE | | | 0.1530 |
| SIMETHICONE | | 0.0120 | |
| TARTARIC ACID | | 0.2600 | |
| ONE OR MORE OF PLANT/ VEGETABLE EXTRACTS, FRAGRANCES, pH ADJUSTERS, VITAMINS, PRESERVATIVES, CHELANTS, SALT (SODIUM CHLORIDE), and/or UV FILTERS | ≤3.0000 | ≤3.0000 | ≤3.0000 |

TABLE 4-continued

Comparative Hair Color Formulations

| INCI NAME | Comparative Formulations | | |
|---|---|---|---|
| | 4A | 4B | 4C |
| WATER and/or PROPYLENE GLYCOL and/or GLYCERIN and/or HEXYLENE GLYCOL and/or CAPRYLYL GLYCOL | Q.S. | Q.S. | Q.S. |
| VISCOSITY | 20-34 UD (86-198 mPa·s) | water thin | 55-85 UD (367-607 mPa·s) |

The viscosities of comparative formulations 4A-4C were evaluated (25° C., 200 RPM, 30 seconds using a spindle #2 (Rheomat 180)) against inventive formulation 1J (Table 1-2), to assess the consistency of the products in order to determine whether the products were suitable for application using the desired applicator, which in this Example employed a squeeze-type plastic bottle having a nozzle-type tip with a diameter ranging from about 0.1 mm to about 0.13 mm. Comparative formulations 4A-4C were either too thin (watery) or too thick (too viscous), and were not suitable for application with the desired applicator, whereas inventive composition 1J had a viscosity that was considered ideal for application with the desired applicator.

Example 5

Comparison of Inventive and Comparative Formulations

The following comparative hair color toning formulation was prepared.

TABLE 5

Comparative Hair Color Toning Formulation

| INCI NAME | Comparative Formulation 5A |
|---|---|
| CETEARYL ALCOHOL | 7.0000 |
| COCOS NUCIFERA (COCONUT) OIL | 0.1000 |
| AMODIMETHICONE | 1.0260 |
| BEHENTRIMONIUM CHLORIDE | 3.1600 |
| CETRIMONIUM CHLORIDE | 0.0180 |
| COCAM IDOPROPYL BETAINE | 3.8000 |
| DISPERSE VIOLET 1 | 0.0175 |
| EXT. VIOLET 2 | 0.0960 |
| CHLORHEXIDINE DIGLUCONATE | 0.0400 |
| ETHANOLAMINE | 0.0350 |
| SCLEROTIUM GUM | 1.0000 |
| SODIUM LIGNOSULFONATE | 0.0325 |
| TRIDECETH-6 | 0.0900 |
| ONE OR MORE OF PLANT/VEGETABLE EXTRACTS, FRAGRANCE, pH ADJUSTERS, VITAMINS, PRESERVATIVES, CHELANTS, SALT (SODIUM CHLORIDE), and/or UV FILTERS | ≤3.0000 |
| WATER and/or ISOPROPYL ALCOHOL and/or PROPYLENE GLYCOL | Q.S. |

In half head studies, bleached and/or color-treated hair on the head of human volunteers (2) was treated on one side with inventive formulation 1J (Table 1-2) and on the other side with comparative formulation 5A. Formulation 1J was left on the hair for 5 minutes, and formulation 5A was left on the hair for 20 minutes. The compositions were rinsed from the hair, which was then blow dried and styled.

It was found that while the hair treated with comparative formulation 5A felt smoother during blow drying and there was ease of blow drying, formulation 5A was less spreadable on the hair compared to inventive formulation 1J, and the color of hair treated with formulation 5A exhibited a warmer tone. On the other hand, the hair treated with inventive formulation 1J felt more soft and silky, had more shine, and had a cooler tone which was more desirable (i.e. less brassiness).

This Example demonstrates that formulations according to the disclosure are more easily applied, impart beneficial cosmetic and sensorial properties, and better hair coloration effects than compositions not according to the disclosure. Notably, the beneficial effects imparted by the inventive formulation were obtained with 5 minute processing times, whereas the comparative composition required 20 minutes of processing in order to achieve the desired degree of coloration.

Example 6

Comparison of Inventive and Comparative Formulations

The following comparative hair color toning formulation was prepared.

TABLE 6

Comparative Hair Color Toning Formulation

| INCI NAME | Comparative Formulation 6A |
|---|---|
| PEG-2 OLEAMINE | 0.1000 |
| POLYQUATERNIUM-11 | 0.4000 |
| GREEN 5 | 0.0006 |
| EXT. VIOLET 2 | 0.0100 |
| SIMETHICONE | 0.0120 |
| TARTARIC ACID | 0.2600 |
| FRAGRANCE, PRESERVATIVES | ≤0.1 |
| WATER | Q.S. |

In a half-head study, bleached and/or color-treated hair on the head of a volunteer was treated on one side with inventive formulation 1J (Table 1-2), and on the other side with comparative formulation 6A. Inventive formulation 1J was applied and left on the hair of one side of the head for 5 minutes and then rinsed off. For the other side of the head, the hair was first treated/contacted with a conventional conditioner, rinsed with water, then treated with comparative formulation 6A, which was left on the hair as a leave-in treatment. The hair was then blow dried and styled.

Inventive formulation 1J was found to have better spreadability on the hair, and provided more body to the hair, while simultaneously providing the hair with a cooler tone (less brassy), compared to comparative formulation 6A which resulted in hair that appeared more limp and weighed down but smoother, with a warmer tone (more brassy).

Overall, inventive formulation 1J provided greater cosmetic benefits and better hair color toning than comparative formulation 6A.

The above data demonstrate that compositions according to the disclosure provide better hair color toning and/or color refreshing benefits to the hair, while simultaneously providing advantageous cosmetic and/or sensorial benefits such as softness, shine, ease of combing/detangling, reduced frizziness, and the like, than the comparative compositions.

The invention claimed is:

1. A hair color toning composition comprising:
   (a) one or more vegetable oils;
   (b) one or more solid fatty alcohols;
   (c) one or more nonionic surfactants;
   (d) one or more non-silicone shine enhancers;
   (e) one or more amidoamines;
   (f) one or more acids;
   (g) one or more direct dyes; and
   (h) water;
   wherein the pH of the composition is from about 2 to about 6, and
   wherein the composition comprises a total amount of direct dyes sufficient to tone the color of hair and/or to minimize the brassiness of color-treated hair and wherein the composition is essentially free of silicones.

2. A hair color toning composition of claim 1, wherein the one or more vegetable oils are chosen from coconut oil, *camellia oleifera* seed oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cede oil, peach kernel oil, coffee bean oil, jojoba oil, and a mixture thereof.

3. A hair color toning composition of claim 1, wherein the total amount of vegetable oils is about 0.5 to about 5% by weight, based on the total weight of the hair color toning composition.

4. A hair color toning composition of claim 1, wherein the one or more solid fatty alcohols are chosen from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol and 2-hexadecyl-1-eicosanol.

5. A hair color toning composition of claim 3, wherein the one or more solid fatty alcohols are chosen from cetearyl alcohol, cetyl alcohol, stearyl alcohol, and a mixture thereof.

6. A hair color toning composition of claim 1, wherein the total amount of solid fatty alcohols is about 1 to about 10% by weight, based on the total weight of the hair color toning composition.

7. A hair color toning composition of claim 1, wherein the one or more nonionic surfactants are esters of polyols with fatty acids or alkoxylated derivatives thereof.

8. A hair color toning composition of claim 5, wherein the one or more nonionic surfactants is chosen from glyceryl distearate, glyceryl hydroxystearate, glyceryl laurate, glyceryl linoleate, glyceryl myristate, glyceryl oleate, glyceryl stearate, an alkoxylated derivate thereof, or a mixture thereof.

9. A hair color toning composition of claim 1, wherein the total amount of the one or more nonionic surfactants is about 0.05 to about 15%, based on the total weight of the hair color toning composition.

10. A hair treatment composition of claim 1, wherein the one or more non-silicone shine enhancers are liquid fatty alcohols.

11. A hair color toning composition of claim 8, wherein the one or more liquid fatty alcohols are chosen from 2-octyldodecanol, isostearyl alcohol, 2-hexyldecanol, 2-heptyldecanol, 2-octyldecanol, caproic alcohol (1-hexanol), enanthic alcohol (1-heptanol), caprylic alcohol (1-octanol), pelargonic alcohol (1-nonanol), capric alcohol (1-decanol), lauryl alcohol (1-dodecanol), and a mixture thereof.

12. A hair color toning composition of claim 1, wherein the total amount non-silicone shine enhancers is about 0.01 to about 10%, based on the total weight of the hair color toning composition.

13. A hair color toning composition of claim 1 comprising one or more amidoamines of the formula:

wherein R is a linear or branched, acyclic alkyl or alkenyl group or an alkyl phenyl group; R' is a divalent hydrocarbon radical containing less than 6 carbon atoms; and R" is H or a hydrocarbon radical containing less than 6 carbon atoms.

14. A hair color toning composition of claim 11, wherein the one or more amidoamines are chosen from oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicamidopropyl dimethylamine, olivamidopropyl dimethylamine, palm itamidopropyl dimethylamine, stearamidoethyldiethylamine, and a mixture thereof.

15. A hair color toning composition of claim 1, wherein the total amount of amidoamines is about 1 to about 15%, based on the total weight of the hair color toning composition.

16. A hair color toning composition of claim 1, wherein the one or more acids are chosen from glycolic acid, lactic acid, malic acid, tartaric acid, citric acid, ascorbic acid, mandelic acid, azelaic acid, glyceric acid, tartronic acid, gluconic acid, benzylic acid, pyruvic acid, 2-hydroxybutyric acid, salicylic acid, trichloroacetic acid, and a mixture thereof.

17. A hair color toning composition of claim 1, wherein the total amount of the one or more acids is about 0.01 to about 5%, based on the total weight of the hair color toning composition.

18. A hair color toning composition of claim 1, wherein the one or more direct dyes are chosen from anionic direct dyes, cationic direct dyes, neutral direct dyes, and a mixture thereof.

19. A hair color toning composition of claim 1, wherein the one or more direct dyes are chosen from HC Blue No. 15, Basic Violet 2, Basic Red 51, HC Violet No. 2, Basic Yellow 87, Basic Orange 31, HC Blue 2, Basic Yellow 57, Ext Violet 2, Acid Red 33, 2-nitro-5-glyceryl methylaniline, 3-methylamino-4-nitrophenoxyethanol, and a mixture thereof.

20. A hair color toning composition of claim 1, wherein the total amount of direct dyes is about 0.01 to about 3% by weight, based on the total weight of the hair color toning composition.

21. A hair color toning composition of claim 1 having a viscosity of greater than 12 DU.

22. A hair color toning composition of claim 1 having a pH of about 3 to about 5.5.

23. A hair color toning composition comprising:
(a) about 1 to about 3% of one or more vegetable oils;
(b) about 2 to about 4% of one or more solid fatty alcohols;
(c) one or more nonionic surfactants;
(d) about 0.1 to about 5% of one or more non-silicone shine enhancers,
wherein the non-silicone shine enhancer is a liquid fatty alcohol;
(e) about 1 to about 15% of one or more amidoamines of the formula:

wherein R is a linear or branched, acyclic alkyl or alkenyl group or an alkyl phenyl group; R' is a divalent hydrocarbon radical containing less than 6 carbon atoms; and R" is H or a hydrocarbon radical containing less than 6 carbon atoms;
(f) about 0.01 to about 5% of one or more acids;
(g) about 0.01 to about 3% of one or more direct dyes; and
(h) about 60 to about 95% of water;
wherein the total amount of direct dyes is sufficient to tone the color of hair and/or to minimize the brassiness of color-treated hair,
all weights being based on the total weight of the hair color toning composition and wherein the composition is essentially free of silicones.

24. A method for toning the color of hair and/or minimizing the brassiness of color-treated hair, comprising applying to the hair a hair color toning composition of claim 1 and optionally rinsing the hair color toning composition from the hair.

25. A method for toning the color of hair and/or minimizing the brassiness of color-treated hair, comprising:
(a) optionally, applying to the hair a shampoo and rinsing the shampoo from the hair;
(b) applying to the hair a hair color toning composition of claim 1; and
(c) optionally, rinsing the hair color toning composition from the hair.

26. The method of claim 25, wherein the method comprises imparting color or tone to hair or minimizing the brassiness of color-treated hair and one or more of:
imparting shine to the hair;
providing smoothness, softness, and/or discipline to the hair;
improving frizz control; and
providing end seal of split ends.

27. A kit comprising:
(a) a hair color toning composition of claim 1;
(b) a shampoo and/or a conditioner and/or a masque treatment;
wherein the hair color toning composition, the shampoo and/or the conditioner and/or the masque treatment are separately contained.

* * * * *

UNITED STATES PATENT AND TRADEMARK OFFICE
CERTIFICATE OF CORRECTION

PATENT NO. : 11,737,964 B2
APPLICATION NO. : 17/389137
DATED : August 29, 2023
INVENTOR(S) : Taylor Katherine Hart et al.

Page 1 of 1

It is certified that error appears in the above-identified patent and that said Letters Patent is hereby corrected as shown below:

In the Claims

Claim 2, Column 38, Line 25, change "cede" to -- cade --; and

Claim 23, Column 40, Line 17, change "RCONHR'N(R")21" to -- RCONHR'N(R")2 --.

Signed and Sealed this
Thirtieth Day of January, 2024

Katherine Kelly Vidal
*Director of the United States Patent and Trademark Office*